(12) United States Patent
Chi et al.

(10) Patent No.: US 11,306,097 B2
(45) Date of Patent: Apr. 19, 2022

(54) ACTIVATION OF CARBONYL BETA-CARBONS FOR CHEMICAL TRANSFORMATIONS

(71) Applicant: Nanyang Technological University, Singapore (SG)

(72) Inventors: Yonggui Chi, Singapore (SG); Zhenqian Fu, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 16/518,839

(22) Filed: Jul. 22, 2019

(65) Prior Publication Data

US 2019/0337955 A1  Nov. 7, 2019

Related U.S. Application Data

(63) Continuation of application No. 14/777,396, filed as application No. PCT/SG2014/000123 on Mar. 14, 2014, now abandoned.

(60) Provisional application No. 61/790,857, filed on Mar. 15, 2013.

(51) Int. Cl.

| C07D 487/04 | (2006.01) |
|---|---|
| C07D 207/28 | (2006.01) |
| C07D 207/26 | (2006.01) |
| C07D 207/50 | (2006.01) |
| C07D 307/36 | (2006.01) |
| C07D 333/06 | (2006.01) |
| C07D 307/33 | (2006.01) |
| C07C 201/12 | (2006.01) |
| C07D 409/04 | (2006.01) |

(52) U.S. Cl.
CPC .......... *C07D 487/04* (2013.01); *C07C 201/12* (2013.01); *C07D 207/26* (2013.01); *C07D 207/28* (2013.01); *C07D 207/50* (2013.01); *C07D 307/33* (2013.01); *C07D 307/36* (2013.01); *C07D 333/06* (2013.01); *C07D 409/04* (2013.01); *C07C 2601/10* (2017.05)

(58) Field of Classification Search
CPC .................................................. C07D 487/04
See application file for complete search history.

(56) References Cited

U.S. PATENT DOCUMENTS 8,143,423 B2   3/2012 Zhang et al.

FOREIGN PATENT DOCUMENTS

| DE | 19704273 A1 | 9/1997 |
| WO | 2007/124484 A2 | 11/2007 |
| WO | 2007/124494 A2 | 11/2007 |

OTHER PUBLICATIONS

Vlahakis et al., Bioorg. Med. Chem., vol. 18, No. 16, Aug. 15, 2010, pp. 6184-6196.*
Ahrendt et al., "New Strategies for Organic Catalysis: The First Highly Enantioselective Organocatalytic Diels—Alder Reaction," *J. Am. Chem. Soc.* 122:4243-4244, 2000.
Ano et al., "Palladium-Catalyzed Direct Ethynylation of C(sp³)—H Bonds in Aliphatic Carboxylic Acid Derivatives," *J. Am. Chem. Soc.* 133:12984-12986, 2011.

(Continued)

*Primary Examiner* — Alicia L Otton
(74) *Attorney, Agent, or Firm* — Seed IP Law Group LLP

(57) ABSTRACT

The present invention relates to a method for synthesizing a compound of Formula (I)

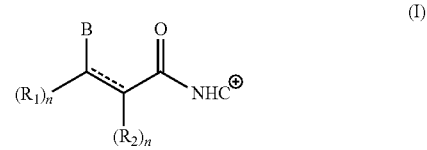

as defined herein, comprising: (i) activating a compound of Formula (II)

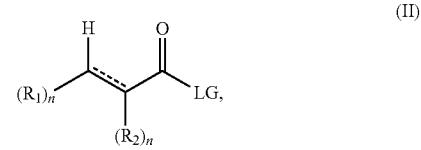

as defined herein, by reacting said compound of Formula (II) with a compound of Formula (III)

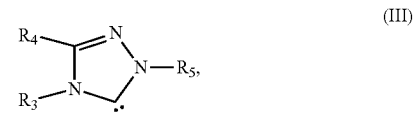

as defined herein, in the presence of a base, to obtain a compound of Formula (IV)

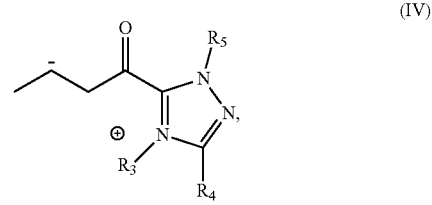

as defined herein; and (ii) reacting the compound of Formula (IV) with an electrophile to obtain the compound of Formula (I). The present invention further relates to the organocatalysts used in the described methods and their respective uses.

12 Claims, No Drawings

(56) References Cited

OTHER PUBLICATIONS

Bantreil et al., "Synthesis of N-heterocyclic carbene ligands and derived ruthenium olefin metathesis catalysts," *Nature Protocols* 6(1):69-77, 2011.
Breslow, "On the Mechanism of Thiamine Action. IV. Evidence from Studies on Model Systems," *J. Am. Chem. Soc.* 80:3719-3726, 1958.
Burstein et al., "Organocatalyzed Conjugate Umpolung of α,β-Unsaturated Aldehydes for the Synthesis of γ-Butyrolactones," *Angew. Chem. Int. Ed.* 43:6205-6208, 2004.
Cardinal-David et al., "Cooperative N-Heterocyclic Carbene/Lewis Acid Catalysis for Highly Stereoselective Annulation Reactions with Homoenolates," *J. Am. Chem. Soc.* 132:5345-5347, 2010.
Chan et al., "Conversion of α, β-Unsaturated Aldehydes into Saturated Esters: An Umpolung Reaction Catalyzed by Nucleophilic Carbenes," *Organic Letters* 7(5):905-908, 2005.
Chan et al., "Direct Amination of Homoenolates Catalyzed by N-Heterocyclic Carbenes," *J. Am. Chem. Soc.* 130(9):S1-S27, 2008.
Chiang et al., "Enantioselective, Cyclopentene-Forming Annulations via NHC-Catalyzed Benzoin—Oxy-Cope Reactions," *J. Am. Chem. Soc.* 129:3520-3521, 2007.
Chiang et al., "α'-Hydroxyenones as Mechanistic Probes and Scope-Expanding Surrogates for α, β-Unsaturated Aldehydes in NHC-Catalyzed Reactions," *J. Am. Chem. Soc.* 131(24):S1-S116, 2009.
Cordova et al., "A Highly Enantioselective Route to Either Enantiomer of Both α- and β-Amino Acid Derivatives," *J. Am. Chem. Soc.* 124(9):1866-1867, 2002.
Diaz et al., "A Stereoselective Synthesis of (R)-(-)-Rolipram from L-Glutamic Acid," *Synthesis*, pp. 559-562, 1997.
Evans et al., "Enantioselective Aldol Condensations. 2. Erythro-Selective Chiral Aldol Condensations via Boron Enolates," *J Am. Chem. Soc.* 103:2127-2129, 1981.
Fang et al., "A Highly Regio- and Stereoselective Cascade Annulation of Enals and Benzodi(enone)s Catalyzed by N-Heterocyclic Carbenes," *Angew. Chem. Int. Ed.* 50:1910-1913, 2011.
Filloux et al., "Multicatalytic, asymmetric Michael/Stetter reaction of salicylaldehydes and activated alkynes," *Proceedings of National Academy of Sciences* 107(48):20666-20671, 2010.
Fu et al., "Controlled β-protonation and [4+2] cycloaddition of enals and chalcones via N-heterocyclic carbene/acid catalysis: toward substrate independent reaction control," *Chem. Commun.* 49:261-263, 2013.
Fu et al., "β-Carbon activation of saturated carboxylic esters through N-heterocyclic carbene organocatalysis," *Nature Chemistry* 5:835-839, 2013.
Giri et al., "Palladium-Catalyzed Methylation and Arylation of $sp^2$ and $sp^3$ C—H Bonds in Simple Carboxylic Acids," *J. Am. Chem. Soc.* 129:3510-3511, 2007.
Gutekunst et al., "Sequential $C_{sp}{}^3$—H Arylation and Olefination: Total Synthesis of the Proposed Structure of Pipercyclobutanamide A," *Angew. Chem. Int. Ed.* 51:7507-7510, 2012.
Hao et al., "Enantioselective Activation of Stable Carboxylate Esters as Enolate Equivalents via N-Heterocyclic Carbene Catalysts," *Org. Lett.* 14(8):2154-2157, 2012.
Jin et al., "Ytterbium triflate catalysed Friedel-Crafts reaction using carboxylic acids as acylating reagents under solvent-free conditions," *Journal of Chemical Research* 10:607-611, 2009.
Kerr et al., "An Efficient Synthesis of Achiral and Chiral 1,2,4-Triazolium Salts: Bench Stable Precursors for N-Heterocyclic Carbenes," *J. Org. Chem* 70:5725-5728, 2005.

Ling et al., "α-Aroyloxyaldehydes: scope and limitations as alternatives to α-haloaldehydes for NHC-catalysed redox transformations," *Chem. Commun.* 47:313-375, 2001.
List "The Direct Catalytic Asymmetric Three-Component Mannich Reaction," *J. Am. Chem. Soc.* 122:9336-9337, 2000.
List et al., "Proline-Catalyzed Direct Asymmetric Aldol Reactions," *J. Am. Chem. Soc.* 122:2395-2396, 2000.
Luo et al., "Palladium/NHC-catalyzed tandem benzylic oxidation/oxidative esterification of benzylic alcohols with phenols," *Tetrahedron* 67:5878-5882, 2011.
Matsuoka et al., "Cyclophane-Type Imidazolium Salts with Planar Chirality as a New Class of N-Heterocyclic Carbene Precursors," *Chem. Eur. J.* 14:9215-9222, 2008.
Mennen et al., "Thiazolylalanine-Derived Catalysts for Enantioselective Intermolecular Aldehyde-Imine Cross-Couplings," *J. Am. Chem. Soc.* 127:1654-1655, 2005.
Mukaiyama et al., "New Aldol Type Reaction," *Chemistry Letters*, pp. 1011-1014, 1973.
Nair et al., "N-Heterocyclic Carbene-Catalyzed Reaction of Chalcones and Enals via Homoenolate: an Efficient Synthesis of 1,3,4-Trisubstituted Cyclopentenes," *J. Am. Chem. Soc.* 128:8736-8737, 2006.
Nakamura et al., "Isolation and Reactions of Titanium Homoenolates of Esters," *J. Am. Chem. Soc.* 105:651-652, 1983.
Nikon et al., "Homoenolate Anions," *J. Am. Chem. Soc.* 84:4604-4605, 1962.
Northrup et al., "The First Direct and Enantioselective Cross-Aldol Reaction of Aldehydes," *J. Am. Chem. Soc.* 124:6798-6799, 2002.
Oba et al., "Synthesis of non-proteinogenic amino acids using Michael addition to unsaturated orthopyroglutamate derivative," *Tetrahedron* 65:128-133, 2009.
Raup et al., "Cooperative catalysis by carbenes and Lewis acids in a highly stereoselective route to γ-lactams," *Nature Chemistry* 2:766-771, 2010.
Reed et al., "β-Substituted β-Phenylpropionyl Chymotrypsins. Structural and Stereochemical Features in Stable Acyl Enzymes," *J. Med. Chem.* 34:1162-1176, 1991.
Renaudat et al., "Palladium-Catalyzed β Arylation of Carboxylic Esters," *Angew. Chem. Int. Ed.* 49:7261-7265, 2010.
Rommel et al., "Cyclic Ketimines as Superior Electrophiles for NHC-Catalyzed Homoenolate Additions with Broad Scope and Low Catalyst Loadings," *J. Am. Chem. Soc.* 130:S1-S86, 2008.
Sarkar et al., "NHC Catalyzed Oxidations of Aldehydes to Esters: Chemoselective Acylation of Alcohols in Presence of Amines," *J. Am. Chem. Soc.* 132:1190-1191, 2010.
Sohn et al., "N-Heterocyclic Carbene-Catalyzed Generation of Homoenolates: γ-Butyrolactones by Direct Annulations of Enals and Aldehydes," *J. Am. Chem. Soc.* 126:14370-14371, 2004.
Thomson et al., "Efficient N-Heterocyclic Carbene-Catalyzed O- to C-Acyl Transfer," *Organic Letters* 8(17):3785-3788, 2006.
Ueno et al., "Nickel-Catalyzed Formation of a Carbon-Nitrogen Bond at the β Position of Saturated Ketones," *Angew. Chem. Int. Ed.* 48:4543-4545, 2009.
Vora et al., "N-Heterocyclic Carbene Catalyzed Asymmetric Hydration: Direct Synthesis of α-Protio and α-Deuterio α-Chloro and α-Fluoro Carboxylic Acids," *J. Am. Chem. Soc.* 132:2860-2861, 2010.
Zaitsev et al., "Highly Regioselective Arylation of $sp^3$ C—H Bonds Catalyzed by Palladium Acetate," *J. Am. Chem. Soc.* 127:13154-13155, 2005.
Zhang et al., "Organocatalytic enantioselective β-funtionalization of aldehydes by oxidation of enamines and their application in cascade reactions," *Nature Communications* 2(211), 2011, 8 pages.

* cited by examiner

ACTIVATION OF CARBONYL BETA-CARBONS FOR CHEMICAL TRANSFORMATIONS

FIELD OF THE INVENTION

The present invention relates to the fields of organocatalytic activation of carbonyl β-carbons to synthesize β-carbon nucleophiles. The present invention is further directed to the organocatalysts used herein and their respective uses.

BACKGROUND

Carbonyl compounds, such as esters, ketones, and aldehydes are essential building blocks in organic chemistry, particularly in the field of pharmaceuticals, fine chemicals, and materials. Therefore, carbonyl compounds are involved in different multistage chemical synthesis. The activation of the α-carbons of carbonyl compounds in order to generate enolate equivalents as nucleophiles is one of the most powerful strategies and commonly used synthesis in organic chemistry including aldol reactions and Mannich reactions. The functionalization of these α-carbons is well known and can be realized via metal-based or organic catalysts or reagents. The most relevant method is directing group-assisted metal insertion and C—H bond activation involving the ester β-carbons using palladium-based transition metal catalysts. As starting material, typically the corresponding α,β-unsaturated carbonyl compounds are used. In contrast herein, the β-carbon of saturated carbonyl compounds is considered to be rather inert. Despite of the fundamental and practical values, direct transformation of β-carbons of saturated carbonyl compounds to nucleophiles is still challenging.

Hence, there is a need in the art for direct activation of carbonyl β-carbons for chemical transformations.

SUMMARY OF THE INVENTION

The present invention provides a method for synthesizing a compound of Formula (I)

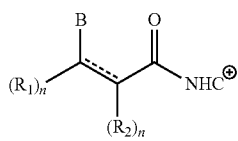
(I)

wherein
═════ a single or a double bond, wherein if it is a double bond n is 1 and if it is a single bond n is 2;
each $R_1$ and $R_2$ is independently selected from the group consisting of hydrogen, halogen, —OH, —OOH, —NH$_2$, —NO$_2$, —ONO$_2$, —CHO, —CN, —CNOH, —COOH, —SH, —OSH, —CSSH, —SCN, —SO$_2$OH, —CONH$_2$, —NH—NH$_2$, —NC, —CSH, or any organic moiety;
B is an electrophilic group; and
NHC$^+$ is

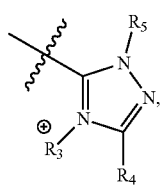

comprising:
(i) activating a compound of Formula (II)

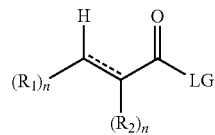
(II)

wherein
LG is a leaving group;
by reacting said compound of Formula (II) with a compound of Formula (III) in the presence of a base

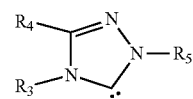
(III)

wherein
$R_3$, $R_4$, and $R_5$ are independently from each other selected from the group consisting of hydrogen, halogen, —OH, —OOH, —NH$_2$, —NO$_2$, —ONO$_2$, —CHO, —CN, —CNOH, —COOH, —SH, —OSH, —CSSH, —SCN, —SO$_2$OH, —CONH$_2$, —NH—NH$_2$, —NC, —CSH, or any organic moiety; to obtain a compound of Formula (IV)

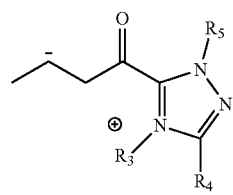
(IV)

and
(ii) reacting the compound of Formula (IV) with an electrophile to obtain the compound of Formula (I).

In another aspect the present invention is directed to compounds of Formulae (VI) and (VII)

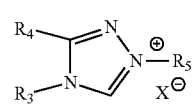
(VI)

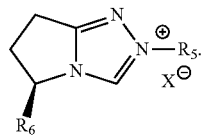
(VII)

wherein $R_3$, $R_4$, $R_5$, and $R_6$ are independently from each other selected from the group consisting of hydrogen, halogen, —OH, —OOH, —NH$_2$, —NO$_2$, —ONO$_2$, —CHO, —CN, —CNOH, —COOH, —SH, —OSH, —CSSH, —SCN, —SO$_2$OH, —CONH$_2$, —NH—NH$_2$, —NC, —CSH, or any organic moiety.

In a still further aspect the present invention relates to the use of compounds of Formulae (VI) and (VII) for activating a compound of Formula (II).

DETAILED DESCRIPTION OF THE PRESENT INVENTION

The present invention is based on the inventors' surprising finding that the β-carbon of a compound of Formula (II) can be activated to transform the compound into a nucleophilic compound of Formula (IV) by organocatalytic activation with a triazol carbene compound of Formula (III) and deprotonation with a base. Without wishing to be bound to any particular theory, it is believed that due to the electron-withdrawing ability of the $NHC^+$ moiety of Formula (III) and the conjugated nature of the compound of formula (IV), the proton(s) attached to the β-carbon become acidic. The obtained nucleophilic compound of Formula (IV) can then further be reacted with an electrophile in order to synthesize a compound of Formula (I).

To obtain β-carbon functionalization, typically the corresponding α,β-unsaturated carbonyl compound is used which is subsequently transformed into the desired nucleophile by, e.g., directing group-assisted transition metal insertion using palladium and C—H bond activation involving the β-carbons. When the saturated compound is the starting material, a further synthetic step is required for converting the saturated carbonyl compound into the corresponding α,β-unsaturated compound. Thus, to functionalize the β-carbon additional synthetic steps involving additional chemicals are necessary and, as a result, complexity of the synthesis procedure and costs are increased.

In contrast to the existing approaches, the present invention provides a cost-effective and less complex strategy for the direct activation of β-carbons of carbonyl compounds without the need for additional synthetic steps and chemicals. The subsequent reaction of the compound of Formula (IV) with an electrophile of interest to yield the desired compound of Formula (I) advantageously provides for high product yields and high selectivity, in particular with respect to enantiomeric ratios.

The inventive synthesis can be conducted at ambient conditions and as a simple one-pot synthesis without purification steps between the synthesis of the compound of Formula (IV) and the subsequent synthesis of the compound of Formula (I).

Based on this finding, in a first aspect the present invention thus relates to a method for synthesizing a compound of Formula (I)

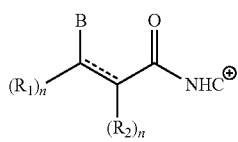

(I)

wherein

╌╌╌╌╌ a single or a double bond, wherein if it is a double bond n is 1 and if it is a single bond n is 2;

each $R_1$ and $R_2$ is independently selected from the group consisting of hydrogen, halogen, —OH, —OOH, —NH$_2$, —NO$_2$, —ONO$_2$, —CHO, —CN, —CNOH, —COOH, —SH, —OSH, —CSSH, —SCN, —SO$_2$OH, —CONH$_2$, —NH—NH$_2$, —NC, —CSH, or any organic moiety;

B is an electrophilic group; and $NHC^+$ is

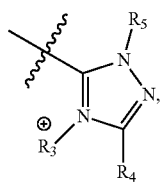

comprising:
(i) activating a compound of Formula (II)

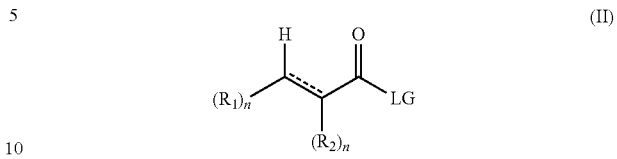

(II)

wherein

LG is a leaving group;

by reacting said compound of Formula (II) with a compound of Formula (III) in the presence of a base

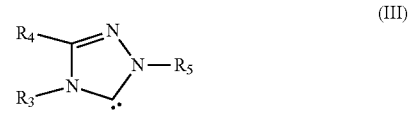

(III)

wherein $R_3$, $R_4$, and $R_5$ are independently from each other hydrogen, halogen, —OH, —OOH, —NH$_2$, —NO$_2$, —ONO$_2$, —CHO, —CN, —CNOH, —COOH, —SH, —OSH, —CSSH, —SCN, —SO$_2$OH, —CONH$_2$, —NH—NH$_2$, —NC, —CSH, or any organic moiety;

to obtain a compound of Formula (IV)

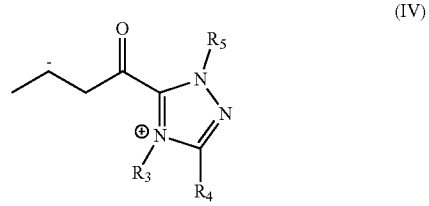

(IV)

and (ii) reacting the compound of Formula (IV) with an electrophile to obtain the compound of Formula (I).

In a preferred embodiment, the compound of Formula (I) can be a saturated carbonyl compound or its corresponding α,β-unsaturated compound. Preferably, the compound of Formula (I) is a saturated carbonyl compound meaning that the bond between the carbon atoms to which $R_1$ and $R_2$ are attached to is a single bond and n is 2. Consequently, the α- and β-carbon atom bear two $R_1$ and $R_2$ moieties, respectively. The two $R_1$ moieties can be selected independently from each other. In other words, the first $R_1$ moiety can be different from the second $R_1$ moiety. The same applies for the $R_2$ moiety.

The term "any organic moiety" as used herein refers to carbon-containing moieties. These moieties can be linear or branched, substituted or unsubstituted, and are preferably derived from hydrocarbons, typically by substitution of one or more hydrogen or carbon atoms by other atoms, such as oxygen, nitrogen, sulfur, phosphorous, or functional groups that contain oxygen, nitrogen, sulfur, phosphorous. The organic moiety can comprise any number of carbon atoms, for example up to up to 5000 or more (typically in case of polymeric moieties), but preferably it is a low molecular weight organic moiety with up to 100, or more preferably up to 40 carbon atoms and, optionally, a molecular weight Mw of 1000 or less. It is preferred that the organic moiety is compatible with the activation reaction described herein and does not adversely affect the described reaction mechanism. Suitable groups and moieties are well known to those skilled in the art or can be readily identified by routine experimentation.

In a preferred embodiment, the organic moiety can be a linear or branched, substituted or unsubstituted alkyl with 1 to x carbon atoms; linear or branched, substituted or unsubstituted alkenyl with 2 to x carbon atoms; linear or branched, substituted or unsubstituted alkinyl with 2 to x carbon atoms; linear or branched, substituted or unsubstituted alkoxy with 1 to x carbon atoms; substituted or unsubstituted cycloalkyl with 3 to x carbon atoms; substituted or unsubstituted cycloalkenyl with 3 to x carbon atoms; substituted or unsubstituted aryl with 6 to x carbon atoms; and substituted or unsubstituted heteroaryl with 3 to x carbon atoms; with x being any integer of 2 or more, preferably up to 50, more preferably up to 30.

In a further embodiment of the present invention, the organic moiety can be a linear or branched, substituted or unsubstituted alkyl with 1 to 40 carbon atoms; linear or branched, substituted or unsubstituted alkenyl with 3 to 40 carbon atoms; linear or branched, substituted or unsubstituted alkoxy with 1 to 40 carbon atoms, substituted or unsubstituted cycloalkyl with 5 to 40 carbon atoms; substituted or unsubstituted cycloalkenyl with 5 to 40 carbon atoms; substituted or unsubstituted aryl with 5 to 40 carbon atoms; and substituted or unsubstituted heteroaryl with 5 to 40 carbon atoms.

In another embodiment, the organic moiety can be a linear or branched, substituted or unsubstituted alkyl with 1 to 20 carbon atoms; linear or branched, substituted or unsubstituted alkenyl with 3 to 20 carbon atoms; linear or branched, substituted or unsubstituted alkoxy with 1 to 20 carbon atoms, substituted or unsubstituted cycloalkyl with 5 to 20 carbon atoms; substituted or unsubstituted cycloalkenyl with 5 to 20 carbon atoms; substituted or unsubstituted aryl with 5 to 14 carbon atoms; and substituted or unsubstituted heteroaryl with 5 to 14 carbon atoms.

The organic moiety can also be a combination of any of the above-defined groups, including but not limited to alkylaryl, arylalkyl, alkylheteroaryl and the like, to name only a few, all of which may be substituted or unsubstituted.

The term "substituted" as used herein in relation to the above moieties refers to a substituent other than hydrogen. Such a substitutent is preferably selected from the group consisting of halogen, —OH, —OOH, —NH$_2$, —NO$_2$, —ONO$_2$, —CHO, —CN, —CNOH, —COOH, —SH, —OSH, —CSSH, —SCN, —SO$_2$OH, —CONH$_2$, —NH—NH$_2$, —NC, —CSH —OR, —NRR', —C(O)R, —C(O)OR, —(CO)NRR', —NR'C(O)R, —OC(O)R, aryl with 5 to 20 carbon atoms, cycloalk(en)yl with 3 to 20 carbon atoms, 3- to 8-membered heterocycloalk(en)yl, and 5- to 20-membered heteroaryl, wherein R and R' are independently selected from hydrogen, alkyl with 1 to 10 carbon atoms, alkenyl with 2 to 10 carbon atoms, alkynyl with 2 to 10 carbon atoms, aryl with 5 to 14 carbon atoms, cycloalk(en)yl with 3 to 20 carbon atoms, 5- to 14-membered heteroaryl, comprising 1 to 4 heteroatoms selected from nitrogen, oxygen, and sulfur, and 5- to 14-membered heterocycloalk(en)yl, comprising 1 to 4 heteroatoms selected from nitrogen, oxygen, and sulfur. Any of these substituents may again be substituted, it is however preferred that these substituents are unsubstituted.

Alkyl refers to a saturated hydrocarbon moiety, such as methyl, ethyl, and the like.

Alkenyl and Alkynyl comprise at least one carbon-carbon double bonds or triple bonds, respectively, and are otherwise defined as alkyl above.

Cycloalkyl refers to a non-aromatic carbocyclic moiety, such as cyclopentanyl, cyclohexanyl, and the like.

Cycloalkenyl refers to non-aromatic carbocyclic compounds that comprise at least one C—C double bond.

Similarly, heterocycloalk(en)yl relates to cycloalk(en)yl groups wherein 1 or more ring carbon atoms are replaced by heteroatoms, preferably selected from nitrogen, oxygen, and sulfur.

Aryl relates to an aromatic ring that is preferably monocyclic or consists of condensed aromatic rings. Preferred aryl substituents are moieties with 6 to 14 carbon atoms, such as phenyl, naphthyl, anthracenyl, and phenanthrenyl.

Heteroaryl refers to aromatic moieties that correspond to the respective aryl moiety wherein one or more ring carbon atoms have been replaced by heteroatoms, such as nitrogen, oxygen, and sulfur.

All of the afore-mentioned groups can be substituted or unsubstituted. When substituted the substituent can be selected from the above list of substituents.

The term "at least one" as used herein relates to one or more, for example 1, 2, 3, 4, 5, 6, 7, 8, 9 or more of the referenced species.

Halogen as used herein refers to F, Cl, Br, and I.

In various embodiments of the present invention, the compound of formula (I) is an α,β-saturated compound, i.e. there is a single bond connecting the α- and β-carbon atom.

In various embodiments of the invention, moiety $R_1$ of Formula (I) and (II) is an alkyl with 1 to 5, preferably 3 carbon atoms.

In various other embodiments, moiety $R_1$ of Formula (I) and (II) is an aryl, selected from the group consisting of phenyl, furane, and naphthalene, which optionally can be substituted, preferably by halogen, alkyl with 1 to 5 carbon atoms, and/or alkoxy with 1 to 5 carbon atoms.

In a further embodiment of the present invention, the compound of Formula (II) is selected from the group consisting of 4-Nitrophenyl 3-(para-tolyl)propanoate, 4-Nitrophenyl 3-(4-methoxyphenyl)propanoate, 4-Nitrophenyl 3-(4-fluorophenyl)propanoate, 4-Nitrophenyl 3-(4-chlorophenyl)propanoate, 4-Nitrophenyl 3-(4-bromophenyl)propanoate, 4-Nitrophenyl 3-(naphthalen-1-yl)propanoate, 4-Nitrophenyl 3-(furan-2-yl)propanoate, 4-Nitrophenyl hexanoate, 4-nitrophenyl 3-(3-(cyclopentyloxy)-4-methoxyphenyl)propanoate, 4-nitrophenyl butyrate, 4-nitrophenyl propionate, and cinammaldehyde.

The term "electrophilic group" as used herein refers to a group that results from the reaction of an electrophile, as described below, with the compound of Formula (IV).

In a preferred embodiment of the present invention, the moieties $R_3$ and $R_4$ of the compound of Formula (III) combine to form together with the carbon atoms to which they are attached a substituted or unsubstituted 5- to 40-membered cycloalkyl, cycloalkenyl, heteroalicyclic, aryl, or heteroaryl ring.

In various embodiments, the compound of Formula (III) is a compound of Formula (V)

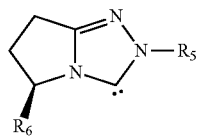

(V)

wherein R$_5$ is as defined above and R$_6$ is selected from the group consisting of hydrogen, halogen, —OH, —OOH, —NH$_2$, —NO$_2$, —ONO$_2$, —CHO, —CN, —CNOH, —COOH, —SH, —OSH, —CSSH, —SCN, —SO$_2$OH, —CONH$_2$, —NH—NH$_2$, —NC, —CSH, or any organic moiety.

R$_6$ can be selected from the group consisting of substituted or unsubstituted, linear or branched alkyl with 1-20 carbon atoms; substituted or unsubstituted, linear or branched alkenyl with 1-20 carbon atoms; substituted or unsubstituted cycloalkyl with 5 to 20 carbon atoms; substituted or unsubstituted cycloalkenyl with 5 to 20 carbon atoms; substituted or unsubstituted aryl with 5-14 carbon atoms; and substituted or unsubstituted heteroaryl with 5-14 carbon atoms. Preferably, R$_6$ is selected from the group consisting of -iso-Pr, -tert-Bu, —CH$_2$Ph, —CH$_2$-iso-Pr, and —CH$_2$-tert-Bu. More preferably, R$_6$ is selected from the group consisting of —CH$_2$-tert-Bu and —CH$_2$-iso-Pr.

In one embodiment of the compound of Formula (V), R$_5$ is aryl. Preferably R$_5$ is selected from the group consisting of phenyl and mesitylene, more preferably R$_5$ is phenyl.

In a preferred embodiment, the compound of Formula (V) is selected from the group consisting of

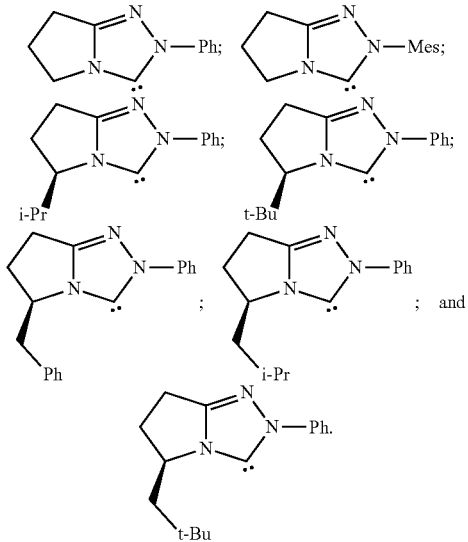

In various embodiments, the compound of Formula (III) or (V) is synthesized from a compound of Formula (VI)

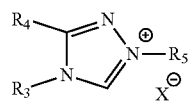

(VI)

wherein X is any anion and R$_3$-R$_5$ are as defined above.

In various embodiments of the present invention, X can be selected from the group consisting of F$^-$, Cl$^-$, Br$^-$, I$^-$, OH$^-$, HSO$_3^-$, SO$_3^{2-}$, SO$_4^{2-}$, NO$_2^-$, NO$_3^-$, PO$_4^{3-}$, BF$_4^-$, PF$_6^-$, ClO$_4^-$, OTf$^-$, acetate, citrate, formiate, glutarate, lactate, malate, malonate, oxalate, pyruvate, and tartrate. In a preferred embodiment of the present invention, X is selected from the group consisting of F$^-$, Cl$^-$, Br$^-$, I$^-$, BF$_4^-$, OTf$^-$, and acetate.

In another embodiment, the compound of Formula (VI) is a compound of Formula (VII)

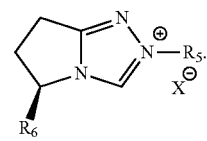

(VII)

wherein R$_5$ and R$_6$ are as defined above.

In still another embodiment of the present invention, the compound of Formula (VII) is selected from the group consisting of

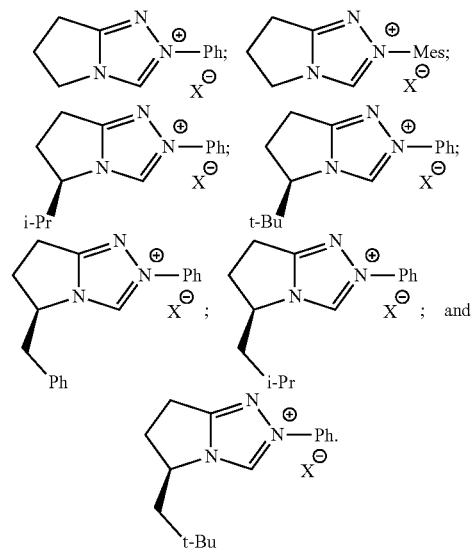

In a preferred embodiment, the compound of Formula (III) or (V) is generated in situ from a compound of Formula (VI) or (VII).

The term "in situ" as used herein means in the reaction mixture. Specifically, this means that the respective compound is synthesized in the reaction mixture.

The term "leaving group" as used herein refers to a moiety that is released from a molecule it was covalently bound to by keeping the pair of electrons previously forming the bond. A leaving group can be a single atom, a molecule, or a functional group. These groups can be an anion or a neutral molecule. The leaving group may have a -I effect. The leaving group of the present invention can be any leaving group which is suitable for the described reaction. In various embodiments, the leaving group can be selected from the group of hydrogen, halogen, -N$_2^+$, —OR$_2^+$, —OSO$_2$C$_4$F$_9$, —OSO$_2$CF$_3$, —OSO$_2$F, —OTs, —OMs, —OH$_2^+$, —OHR$^+$, —ONO$_2$, —OPO(OH)$_2$, —SR$_2$, —NR$_3$, —OCOR, —NH$_3^+$, and —O—C$_6$H$_4$-para-NO$_2$, and R can be any organic residue or moiety. In a preferred embodiment, the leaving group is —O—C$_6$H$_4$-para-NO$_2$.

The reactions can be carried out in an organic solvent. The organic solvent used in the present invention can be any organic solvent which is suitable. In a preferred embodiment, the organic solvent is selected from the group consisting of tert-Butanol, toluene, THF, $CH_3CN$, $CH_2Cl_2$, dioxane, ethyl acetate, and mixtures thereof. For the different steps of (i), i.e. activating a compound of Formula (I), and (ii), i.e. reacting the compound of Formula (IV) with an electrophile, different or the same organic solvents can be used.

In various embodiments, both steps (i) and (ii) are conducted in a one-pot synthesis.

The term "one-pot synthesis" as used herein means that the reactions (i) and (ii) according to the present invention are carried out in the same reaction vessel without any purification step of an intermediate.

In various embodiments, the base in the reaction mixture is present in an amount of 100 to 300 mol-%, preferably 115 to 250 mol-%, more preferably 130 to 200 mol-%, most preferably about 150 mol-%, based on the total amount of the compound of Formula (I).

"About", as used herein, refers to the numerical value it relates to ±10%.

In various embodiments of the present invention, the electrophile can be any suitable electrophile. "Electrophile", as used herein, generally relates to any reagent, such as atom or molecule, that is attracted to electrons and participates in the chemical reaction by accepting an electron pair in order to bind to the nucleophile. In various embodiments, the electrophile may be a Lewis acid. In preferred embodiments, the electrophile is selected from the group consisting of $F_2$, $Cl_2$, $Br_2$, $I_2$, alkyl-LG, alkenyl-LG, alkoxy-LG, acyl-LG, aryl-LG, heteroaryl-LG, hydrazone, and a carbonyl compound. "LG" is a leaving group and is defined as above. The electrophile can also be any Michael acceptor.

In specific embodiments, the electrophile is selected from the group of optionally α,β-unsaturated, linear or branched, substituted or unsubstituted ketone; optionally α,β-unsaturated, linear or branched, substituted or unsubstituted aldehyde; optionally α,β-unsaturated, linear or branched, substituted or unsubstituted esters; optionally α,β-unsaturated, linear or branched, substituted or unsubstituted trifluoroketone; optionally α,β-unsaturated, linear or branched, substituted or unsubstituted carboxamide; optionally α,β-unsaturated, linear or branched, substituted or unsubstituted amide; optionally α,β-unsaturated, linear or branched, substituted or unsubstituted nitrile; optionally linear or branched, substituted or unsubstituted imine; linear or branched, substituted or unsubstituted nitrone; linear or branched, substituted or unsubstituted diazene, and optionally α,β-unsaturated, linear or branched, substituted or unsubstituted hydrazone. More preferably, the electrophile is selected from the group consisting of α,β-unsaturated, linear or branched, substituted or unsubstituted ketone, trifluoroketone, and hydrazone.

In various embodiments, the base used in accordance with the present invention contains one or more nitrogen atom(s). The base used can be any suitable base and may, for example, be selected from the group consisting of pyrrolidine; $N(CH_3)_3$; $N(CH_2CH_3)_3$; (iso-Propyl)$_2$NH; 2,2,6,6-Tetramethyl-1-piperidin; LDA (Lithium diisopropylamid); LHMDS (Lithium bis(trimethylsilyl)amide); LTMP (Lithium tetramethylpiperidide); and 4-aminopyridine.

In a preferred embodiment, the base is an amidine. The amidine can be selected from the group consisting of DBU (1,8-Diazabicyclo[5.4.0]undec-7-en); DBN (1,5-Diazobicyclo[3.4.0]non-5-ene); and DABCO (1,4-Diazobicyclo[2.2.2]octan).

In another embodiment of the present invention, the base is a phosphazine. The phosphazine can be selected from the group consisting of $P_1$-tert-Bu-tris(tetramethylene); 2-tert-Butylimino-2-diethylamino-1,3-dimethylperhydro-1,3,2-diazaphosphorine; and 1-Ethyl-2,2,4,4,4-pentakis(dimethylamino)-2$\lambda^5$, 4$\lambda^5$-catenadi(phosphazene).

In various embodiments, the reaction temperature used in steps (i) and (ii) of the method disclosed herein ranges from 0° C. to 85° C. The reaction temperature of these steps can also be from 15° C. to 55° C. Preferably, the reaction temperature used in steps (i) and (ii) is about 20 to 30° C., more preferably about 25° C.

The reaction temperatures of steps (i) and (ii) may be selected independently from each other, for instance the reaction temperature of step (i) may be 25° C. whereas the reaction temperature of step (ii) may be 40° C.

In various embodiments of the invention, the reaction time is from 0.1 hours to 72 hours. The reaction time can also be from 1 hour to 48 hours. In still another embodiment, the reaction time is from 5 hours to 36 hours, preferably about 24 hours.

In various embodiments of the present invention, a molecular sieve is present in the reaction mixture, preferably with apertures of a size of approximately 4 Å.

The method disclosed herein may comprise additional reaction steps which may be carried out after or between the reaction steps (i) and (ii) according to the present invention. Such additional steps may include steps for catalyst regeneration, Michael reactions, aldol reactions, lactonization, and/or decarboxylation.

The present invention also encompasses a compound of Formula (VI) or (VII).

In various embodiments, the compound of Formula (VI) or (VII) may be selected from the group consisting of

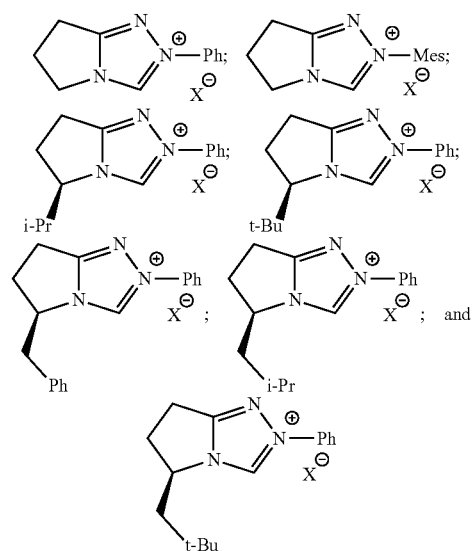

wherein X is defined as above.

Also encompassed by the present invention is the use of a compound of Formula (VI) or (VII) for activating a compound of Formula (II), wherein said compounds are as defined above.

In various embodiments, for this use the compound of Formula (VI) or (VII) is selected from the group consisting of

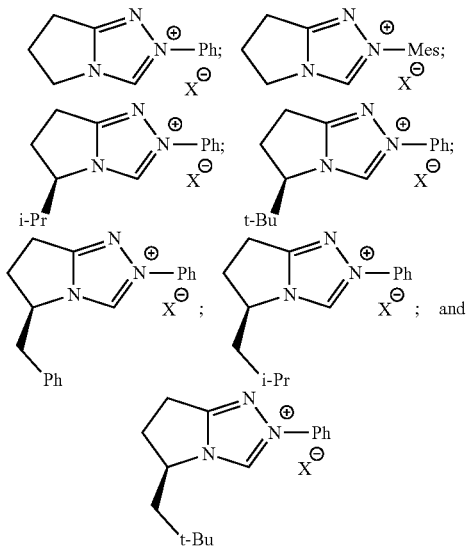

wherein X is defined as above.

By "comprising", as used herein, is meant including, but not limited to, whatever follows the word "comprising". Thus, use of the term "comprising" indicates that the listed elements are required or mandatory, but that other elements are optional and may or may not be present.

The following examples are provided to better illustrate the claimed invention and are not be interpreted in any way as limiting the scope of the invention. All specific compounds, materials, and methods described below, in whole or in part, fall within the scope of the invention. These specific compounds, materials, and methods are not intended to limit the invention, but merely to illustrate specific embodiments falling within the scope of the invention. One skilled in the art may develop equivalent compounds, materials, and use without the exercise of inventive capacity and without departing from the scope of the invention. It is the intention of the inventors that such variations are included in the scope of the present invention.

All references cited herein are incorporated by reference in their entirety.

EXAMPLES

General Information

Commercially available materials purchased from Alfa Aesar or Sigma-Aldrich were used as received. HPLC grade $CH_3CN$ (purchased from TEDIA) was dried over 4 Å molecular sieve prior use. Toluene and DCM was dried over Pure Solv solvent purification system. THF was distilled over sodium. Other solvents were dried over 4 Å molecular sieve prior use. Proton nuclear magnetic resonance ($^1$H-NMR) spectra were recorded on a Bruker (400 MHz) spectrometer. Chemical shifts were recorded in parts per million (ppm, δ) relative to tetramethylsilane (δ=0.00) or chloroform (δ=7.26, singlet). $^1$H NMR splitting patterns are designated as singlet (s), doublet (d), triplet (t), quartet (q), dd (doublet of doublets); m (multiplets), and etc. All first-order splitting patterns were assigned on the basis of the appearance of the multiplet. Splitting patterns that could not be easily interpreted are designated as multiplet (m) or broad (br). Carbon nuclear magnetic resonance ($^{13}$C-NMR) spectra were recorded on a Bruker (400 MHz) (100 MHz) spectrometer. High resolution mass spectral analysis (HRMS) was performed on Finnigan MAT 95 XP mass spectrometer (Thermo Electron Corporation). The determination of enantiomeric excess was performed via chiral HPLC analysis using Shimadzu LC-20AD HPLC workstation. X-ray crystallography analysis was performed on Bruker X8 APEX X-ray diffractionmeter. Optical rotations were measured using a 1 mL cell with a 1 dm path length on a Jasco P-1030 polarimeter and are reported as follows: $[\alpha]^{rt}_D$ (c is in gm per 100 mL solvent). Analytical thin-layer chromatography (TLC) was carried out on Merck 60 F254 pre-coated silica gel plate (0.2 mm thickness). Visualization was performed using a UV lamp or potassium permanganate stain.

Substrate Preparation

The synthesis of 4-nitrophenyl esters (1b-i) was performed by adopting known procedures.[1]

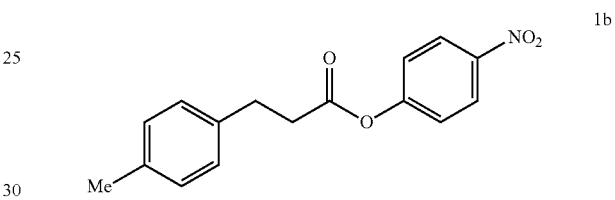

4-Nitrophenyl 3-(para-tolyl)propanoate: White solid; 69% yield; $^1$H NMR (400 MHz, CDCl$_3$) δ=2.34 (s, 3H), 2.91 (t, J=7.6 Hz, 2H), 3.04 (t, J=7.6 Hz, 2H), 7.12-7.25 (m, 6H), 8.22-8.26 (m, 2H); $^{13}$C NMR (100 MHz, CDCl$_3$) δ=170.5, 155.4, 145.3, 136.6, 136.2, 129.4, 128.3, 125.2, 122.5, 36.1, 30.4, 21.1; HRMS(ESI) calcd for $C_{16}H_{16}NO_4$ (M+H)$^+$: 286.1079, Found: 286.1088.

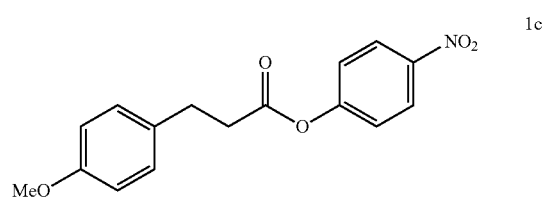 [SMILES: COc1ccc(CCC(=O)Oc2ccc([N+](=O)[O-])cc2)cc1]

4-Nitrophenyl 3-(4-methoxyphenyl)propanoate: White solid; 88% yield; $^1$H NMR (400 MHz, CDCl$_3$) δ=2.90 (t, J=7.2 Hz, 2H), 3.02 (t, J=7.2 Hz, 2H), 3.80 (s, 3H), 6.87 (d, J=8.8 Hz, 2H), 7.18-7.26 (m, 4H), 8.24 (d, J=8.8 Hz, 2H); $^{13}$C NMR (100 MHz, CDCl$_3$) δ=170.5, 158.4, 155.4, 145.3, 131.7, 129.4, 125.2, 122.5, 114.1, 55.3, 36.2, 30.0; HRMS (ESI) calcd for $C_{16}H_{16}NO_5$ (M+H)$^+$: 302.1028, Found: 302.1032.

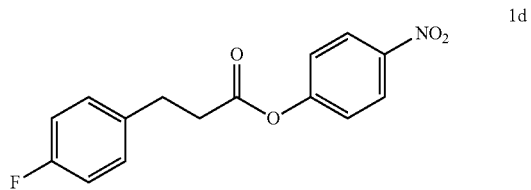 [SMILES: O=C(CCc1ccc(F)cc1)Oc1ccc([N+](=O)[O-])cc1]

4-Nitrophenyl 3-(4-fluorophenyl)propanoate: White solid; 87% yield; $^1$H NMR (400 MHz, CDCl$_3$) δ=2.89-2.93 (m, 2H), 3.06 (t, J=7.2 Hz, 2H), 6.99-7.04 (m, 2H), 7.17-7.24 (m, 4H), 8.23-8.27 (m, 2H); $^{13}$C NMR (100 MHz, CDCl$_3$) δ=170.3, 162.9, 160.5, 155.3, 145.4, 135.4, 135.3, 129.9, 129.8, 125.2, 122.4, 115.6, 115.4, 36.0, 30.0; HRMS (ESI) calcd for C$_{15}$H$_{13}$FNO$_4$ (M+H)$^+$: 290.0829, Found: 290.0841.

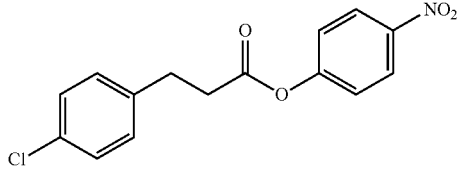

1e

4-Nitrophenyl 3-(4-chlorophenyl)propanoate: White solid; 90% yield; $^1$H NMR (400 MHz, CDCl$_3$) δ=2.90-2.94 (m, 2H), 3.05 (t, J=7.2 Hz, 2H), 7.18-7.31 (m, 6H), 8.25 (d, J=9.2 Hz, 2H); $^{13}$C NMR (100 MHz, CDCl$_3$) δ=170.2, 155.3, 145.4, 138.1, 132.5, 129.8, 128.8, 125.2, 122.4, 35.7, 30.1; HRMS(ESI) calcd for C$_{15}$H$_{13}$ClNO$_4$ (M+H)$^+$: 306.0533, Found: 306.0542.

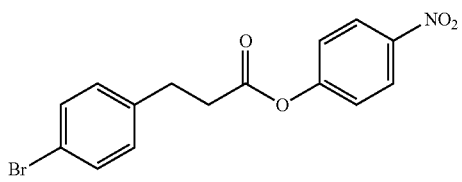

1f

4-Nitrophenyl 3-(4-bromophenyl)propanoate: White solid; 83% yield; $^1$H NMR (400 MHz, CDCl$_3$) δ=2.90-2.94 (m, 2H), 3.03 (t, J=7.2 Hz, 2H), 7.13-7.22 (m, 4H), 7.45 (d, J=7.2 Hz, 2H), 8.23-8.26 (m, 2H); $^{13}$C NMR (100 MHz, CDCl$_3$) δ=170.2, 155.3, 145.4, 138.7, 131.8, 130.2, 125.2, 122.4, 120.5, 35.7, 30.1; HRMS(ESI) calcd for C$_{15}$H$_{13}$BrNO$_4$Na (M+Na)$^+$: 371.9847, Found: 371.9846.

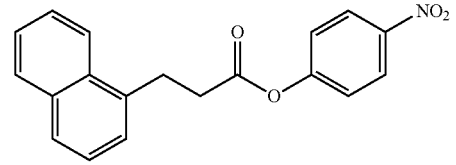

1g

4-Nitrophenyl 3-(naphthalen-1-yl)propanoate: White solid; 83% yield; $^1$H NMR (400 MHz, CDCl$_3$) δ=3.06 (t, J=7.6 Hz, 2H), 3.54 (t, J=7.6 Hz, 2H), 7.15-7.19 (m, 2H), 7.40-7.58 (m, 4H), 7.77 (dd, J=7.2, 2.4 Hz, 1H), 7.88-7.90 (m, 1H), 8.05 (d, J=8.4 Hz, 1H), 8.20-8.24 (m, 2H); $^{13}$C NMR (100 MHz, CDCl$_3$) δ=170.6, 155.4, 145.4, 135.7, 134.0, 131.6, 129.1, 127.6, 126.4, 126.3, 125.8, 125.6, 125.2, 123.2, 122.4, 35.3, 28.0; HRMS(ESI) calcd for C$_{19}$H$_{16}$NO$_4$ (M+H)$^+$: 322.1079, Found: 322.1093.

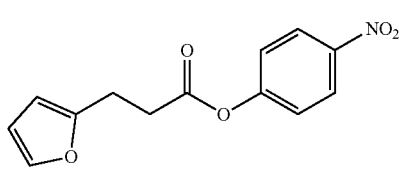

1h

4-Nitrophenyl 3-(furan-2-yl)propanoate: White solid; 80% yield; $^1$H NMR (400 MHz, CDCl$_3$) δ=2.94-2.97 (m, 2H), 3.11 (t, J=7.2 Hz, 2H), 6.10 (dd, J=3.2, 0.4 Hz, 1H), 6.32 (dd, J=3.2, 1.6 Hz, 1H), 7.23-7.27 (m, 2H), 7.35 (d, J=1.2 Hz, 1H), 8.24-8.28 (m, 2H); $^{13}$C NMR (100 MHz, CDCl$_3$) δ=170.1, 155.4, 153.3, 145.4, 141.6, 125.2, 122.4, 110.4, 105.9, 33.0, 23.4; HRMS(ESI) calcd for C$_{13}$H$_{12}$NO$_5$ (M+H)$^+$: 262.0715, Found: 262.0710.

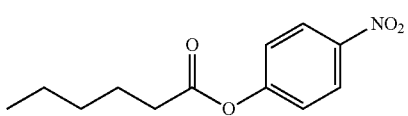

1i

4-Nitrophenyl hexanoate: colorless liquid; 95% yield; $^1$H NMR (400 MHz, CDCl$_3$) δ=0.94 (t, J=7.2 Hz, 3H), 1.36-1.43 (m, 4H), 1.76 (q, J=7.6 Hz, 2H), 2.60 (t, J=7.2 Hz, 2H), 7.27-7.29 (m, 2H), 7.26 (d, J=8.8 Hz, 2H); $^{13}$C NMR (100 MHz, CDCl$_3$) δ=171.3, 155.6, 145.3, 125.2, 122.4, 34.3, 31.2, 24.4, 22.3, 13.9; HRMS(ESI) calcd for C$_{12}$H$_{16}$NO$_4$ (M+H)$^+$: 238.1079, Found: 238.1079.

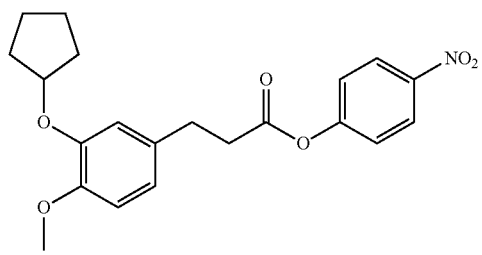

1j 4-nitrophenyl 3-(3-(cyclopentyloxy)-4-methoxyphenyl)propanoate: yellow oil; 90% yield; $^1$H NMR (400 MHz, CDCl$_3$) δ=1.55-1.62 (m, 2H), 1.84-1.91 (m, 6H), 2.90 (t, J=7.2 Hz, 2H), 3.01 (t, J=7.2 Hz, 2H), 3.84 (s, 3H), 4.73-4.76 (m, 1H), 6.76-6.84 (m, 3H), 7.19 (d, J=8.8 Hz, 2H), 8.25 (d, J=8.8 Hz, 2H); $^{13}$C NMR (100 MHz, CDCl$_3$) δ=170.5, 155.4, 148.9, 147.8, 145.3, 132.1, 125.2, 122.4, 120.3, 115.6, 112.2, 80.5, 56.2, 36.2, 32.8, 30.4, 24.0; HRMS(ESI) calcd for C$_{21}$H$_{24}$NO$_6$ (M+H)$^+$: 386.1604, Found: 386.1603.

Catalytic Preparation

The triazolium-based compound of Formulae (III) and (V) (A-H) were prepared by adopting known procedures.[2]

D

Example 1: (R)-5-Isopropyl-2-phenyl-6,7-dihydro-5H-pyrrolo[2,1-c][1,2,4]triazol-2-ium tetrafluoroborate: White solid; $[\alpha]_D^{23}$ (c 2.0, $CH_3CN$)=+49.6°; $^1H$ NMR (400 MHz, $CDCl_3$) δ 0.91 (d, J=6.8 Hz, 3H), 1.04 (d, J=6.8 Hz, 3H), 2.42-2.59 (m, 2H), 2.88-2.98 (m, 1H), 3.09-3.18 (m, 1H), 3.22-3.30 (m, 1H), 4.89-4.94 (m, 1H), 7.48-7.54 (m, 3H), 7.86 (d, J=6.8 Hz, 2H), 10.09 (s, 1H); $^{13}C$ NMR (100 MHz, $CDCl_3$) δ 162.2, 136.9, 135.6, 130.7, 130.1, 120.8, 66.2, 31.1, 28.4, 21.7, 18.4, 16.2; HRMS(ESI) calcd for $C_{14}H_{18}N_3$ $(M)^+$: 228.1501, Found: 228.1496.

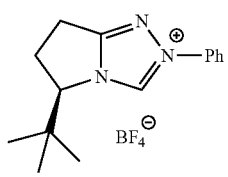

Example 2: (R)-5-(Tert-butyl)-2-phenyl-6,7-dihydro-5H-pyrrolo[2,1-c][1,2,4]triazol-2-ium tetrafluoroborate: White solid; $[\alpha]_D^{23}$ (c 2.0, $CH_3CN$)=+45.4°; $^1H$ NMR (400 MHz, $CDCl_3$) δ 1.04 (s, 9H), 2.58-2.65 (m, 1H), 2.94-3.22 (m, 3H), 4.75-4.77 (m, 1H), 7.49-7.55 (m, 3H), 7.88 (d, J=7.2 Hz, 2H), 10.01 (s, 1H); $^{13}C$ NMR (100 MHz, $CDCl_3$) δ 162.7, 137.5, 135.5, 130.7, 130.1, 121.0, 70.5, 34.6, 29.0, 25.6, 21.7; HRMS(ESI) calcd for $C_{15}H_{20}N_3(M)^+$: 242.1657, Found: 242.1655.

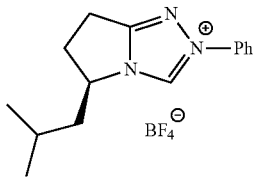

Example 3: (R)-5-Isobutyl-2-phenyl-6,7-dihydro-5H-pyrrolo[2,1-c][1,2,4]triazol-2-ium tetrafluoroborate: White solid; $[\alpha]_D^{23}$ (c 2.0, $CH_3CN$)=+40.7°; $^1H$ NMR (400 MHz, $CDCl_3$) δ 0.97-1.00 (m, 6H), 1.59-1.75 (m, 2H), 2.14-2.20 (m, 1H), 2.42-2.47 (m, 1H), 3.02-3.07 (m, 1H), 3.19-3.29 (m, 2H), 4.99-5.03 (m, 1H), 7.47-7.52 (m, 3H), 7.81-7.84 (m, 2H), 10.05 (s, 1H); $^{13}C$ NMR (100 MHz, $CDCl_3$) δ 161.7, 136.6, 135.6, 130.6, 130.1, 120.8, 60.2, 42.9, 33.3, 25.2, 22.9, 21.6, 21.3; HRMS(ESI) calcd for $C_{15}H_{20}N_3$ $(M)^+$: 242.1657, Found: 242.1657.

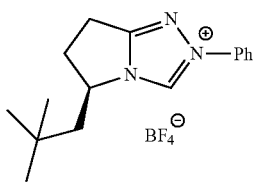

Example 4: (R)-5-Neopentyl-2-phenyl-6,7-dihydro-5H-pyrrolo[2,1-c][1,2,4]triazol-2-ium tetrafluoroborate: White solid; $[\alpha]_D^{23}$ (c 2.0, $CH_3CN$)=+48.2°; $^1H$ NMR (400 MHz, $CDCl_3$) δ 0.99 (s, 9H), 1.67 (dd, J=13.6, 11.2 Hz, 1H), 2.36 (dd, J=12.8, 2.0 Hz, 1H), 2.45-2.51 (m, 1H), 3.08-3.22 (m, 2H), 3.27-3.36 (m, 1H), 4.98-5.01 (m, 1H), 7.45-7.51 (m, 3H), 7.81-7.83 (m, 2H), 10.03 (s, 1H); $^{13}C$ NMR (100 MHz, $CDCl_3$) δ 161.4, 136.5, 135.6, 130.5, 130.1, 120.8, 59.8, 48.2, 35.8, 30.4, 29.7, 22.1; HRMS(ESI) calcd for $C_{16}H_{22}N_3$ $(M)^+$: 256.1814, Found: 256.1812.

General Procedure of the Catalytic Reactions

Example 5: Reaction of esters and enones to synthesize 3 (3a as an example): A dry 10 mL Schlenk tube equipped with a magnetic stirring bar was successively charged with ester 1a (109 mg, 0.40 mmol), chalcone 2a (42 mg, 0.20 mmol), NHC pre-catalyst H (13.8 mg, 0.04 mmol) and 4 Å Molecular Sieve (200 mg). The tube was closed with a septum, evacuated, and refilled with nitrogen. To this mixture was added dry $CH_3CN$ (0.5 mL), followed by the addition of DBU (46 μL, 0.30 mmol) via a micro syringe. After stirred for 24 hours at room temperature, the reaction mixture was analyzed by $^1H$ NMR analysis (to determine d.r.), and then directly applied to silica gel column chromatography (1% v/v ethyl acetate in hexane) to afford 3a as a colorless oil in 66% yield, 7:1 d.r. and 95:5 e.r.

Example 6: The synthesis γ-lactone 5a from ester 1a and trifluoroketone 4a was performed using a procedure similar to that used in the catalytic synthesis of 3a: A dry 10 mL Schlenk tube equipped with a magnetic stirring bar was successively charged with ester 1a (109 mg, 0.40 mmol), 2,2,2-trifluoro-1-phenylethanone 4a (28 μL, 0.20 mmol), NHC pre-catalyst H (13.8 mg, 0.04 mmol) and 4 Å Molecular Sieve (200 mg). The tube was closed with a septum, evacuated, and refilled with nitrogen. To this mixture was added dry toluene (1.0 mL), followed by the addition of DBU (46 μL, 0.30 mmol) via a micro syringe. After stirred for 48 hours at 0° C., the reaction mixture was concentrated under reduced pressure. The crude residue was analyzed by $^1H$ NMR analysis (to determine d.r.), and then directly applied to silica gel column chromatography (2:1 v/v hexanes/dichloromethane) to afford γ-lactone products-a mixture of diastereomers (5a, and 5a') as a colorless oil in 54% yield with 1.3:1 d.r., 91:9 and 94:6 e.r. for the major and minor diastereomer respectively. For the trans- and cis-isomers, (4S, 5S)-5a and (4S, 5R)-5a' were obtained as the major enantiomers respectively. The relative and absolute chemistry were determined by comparing the chiral phase HPLC trace with authentic samples prepared using literature methods.[3] HPLC (Chiralcel OD, 99:1 hexanes/i-PrOH, 0.7 mL/min), $t_r$ (5a-major)=22.6 min, $t_r$ (5a-minor)=42.3 min, $t_r$ (5a'-major)=20.0 min, $t_r$ (5a'-minor)=68.7 min.

TABLE S1

Organocatalytic approach to activate saturated ester β-carbon as nucleophile for asymmetric reaction.

| Entry | Compound of Formula (VI) | 3a:4a | 3a yield | 3a d.r. | 3a e.r. |
|---|---|---|---|---|---|
| 1 | A | n.d. | <5 | n.d | — |
| 2 | B | >20:1 | 85 | 14:1 | — |
| 3 | C | 5:1 | 79 | 7:1 | — |
| 4 | D | >20:1 | 69 | 11:1 | 87:13 |
| 5 | E | >20:1 | 30 | 8:1 | 95:5 |
| 6 | F | 8:1 | 54 | 16:1 | 87:13 |
| 7 | G | >20:1 | 71 | 12:1 | 91:9 |
| 8* | G | >20:1 | 74 | 14:1 | 91:9 |
| 9* | H | >20:1 | 70(66) | 7:1 | 95.5:4.5 |

Unpurified reaction mixture. The enantiomeric ratio (e.r.) of 3a (major diastereomer) was determined via chiral phase HPLC analysis, absolute configuration of 3a was determined via X-ray structure of 3y. Structure of a-activation product 4a was confirmed via $^1$H NMR analysis.
*Reactions run with 150 mol. % DBU, yield for 3a in parentheses (entry 9) was isolated yield.
NHC, N-heterocyclic carbene.
DBU, 1,8-diazabicyclo[5.4.0]undec-7-ene.
MS, molecular sieve.
Mes, 1,3,5-trimethylbenzene.
i-Pr, iso-propyl.
t-Bu, tert-butyl.

TABLE S2

Condition optimization for synthesis of γ-lactone 5a and 5a' from ester 1a and triflouroketone 4a

| Entry | Solvent | Temperature | Time (h) | Yield (5a + 5a') (%)[a] | d.r. (5a:5a')[b] | e.r.[c] |
|---|---|---|---|---|---|---|
| 1 | CH$_2$Cl$_2$ | RT | 24 | 61 | 2.1:1 | 77:23/79:22 |
| 2 | Toluene | RT | 24 | 56 | 1.3:1 | 89:11/92:8 |
| 3 | CH$_3$CN | RT | 24 | 58 | 1.8:1 | 75:25/79:22 |
| 4 | Ethyl Acetate | RT | 24 | 58 | 1.4:1 | 86:14/91:9 |
| 5 | THF | RT | 24 | 57 | 1.3:1 | 86:14/91:9 |
| 6 | t-BuOH | RT | 24 | 73 | 3.0:1 | 72:28/75:25 |
| 7 | Dioxane | RT | 24 | 49 | 1.4:1 | 87:13/90:10 |

TABLE S2-continued

Condition optimization for synthesis of γ-lactone 5a and 5a' from ester 1a and triflouroketone 4a R = Ph, 1a (0.4 mmol) + Ar = Ph, 4a (0.2 mmol), 20 mol. % H, 150 mol. % DBU, toluene (0.2M), 4A MS, 0° C., 48 h → 5a + 5a' (R = Ar = Ph)

| Entry | Solvent | Temperature | Time (h) | Yield (5a + 5a') (%)[a] | d.r. (5a:5a')[b] | e.r.[c] |
|---|---|---|---|---|---|---|
| 8 | Toluene. | 0° C. | 24 | 45 | 1.3:1 | 91:9/94:6 |
| 9 | Toluene. | 0° C. | 48 | 54 | 1.3:1 | 91:9/94:6 |

[a]Isolated yield.
[b]Diastereomeric ratio, estimated via $^1$H NMR analysis of crude reaction mixture.
[c]Enatiomeric ratio of 5a and 5a' respectively, estimated via chiral phase HPLC analysis.
RT, room temperature, which is 25° C.

Example 7: The synthesis of γ-lactam 7a and 7a' from ester 1a and hydrazone 6a was performed using a similar procedure to that for the preparation of 5a above: A dry 10 mL Schlenk tube equipped with a magnetic stir bar was successively charged with ester 1a (55 mg, 0.2 mmol), hydrazone 6a (22 mg, 0.10 mmol), NHC pre-catalyst H (6.9 mg, 0.02 mmol) and 4 Å Molecular Sieve (200 mg). The tube was closed with a septum, evacuated, and refilled with nitrogen. To this mixture was added dry EA (0.5 mL), followed by the addition of DBU (23 μL, 0.15 mmol) via a micro syringe. After being stirred for 48 hours at 40° C., the reaction mixture was concentrated under reduced pressure. The crude residue was analyzed by $^1$H NMR analysis (to determine d.r.), and then was diluted with $CH_2Cl_2$ (15 mL) and washed with a 1:1 mixture of saturated aqueous $NH_4Cl$ and water (10 mL). The aqueous layer was extracted with $CH_2Cl_2$ (2×15 mL) and the combined organic layers were dried over anhydrous sodium sulfate, filtered, and concentrated. The oily residue was applied to silica gel column chromatography (3:1 v/v hexanes/ethyl acetate) to afford γ-lactam products-a mixture of diastereomers as a colorless oil in 74% yield with 6:1 d.r., 97:3/90:10 e.r. for the major and minor diastereomers respectively. The two diastereomers could also be separated for HPLC, NMR, and optical rotation analysis. The relative stereo-configurations of both diastereomers were determined by comparison with literature samples,[4] and the absolute configuration of the trans-isomer (7a) was determined via x-ray structure analysis. HPLC [Chiralcel IA, 75:20:5 hexanes/(hexanes:i-PrOH: $CH_3OH$=75:20:5)/i-PrOH, 0.7 mL/min], $t_r$ (7a-major)=88.3 min, $t_r$ (7a-minor)=110.2 min, $t_r$ (major enantiomer of the minor diastereomer)=66.7 min, $t_r$ (minor enantiomer of the minor diastereomer)=72.9 min. Optical rotation: 7a, $[\alpha]_D^{23}$ (c 0.94, $CH_2Cl_2$)=−39.1°.

TABLE S3

Condition optimization for synthesis of γ-lactam 7a from ester 1a and hydrazone 6a 1a (0.2 mmol) + 6a (0.1 mmol), 20 mol. % H, 150 mol. % DBU, 40° C., 48 h → 7a

| Entry[a] | Solvent | Yield (%)[b] | d.r.[c] | e.r.[d] |
|---|---|---|---|---|
| 1 | $CH_3CN$ | 26 | 3.3:1 | 98:2/91:9 |
| 2 | Toluene | 72 | 5.8:1 | 97:3/89:11 |
| 3 | Dioxane | 95 | 3.6:1 | 97:3/90:10 |
| 4 | Ethyl Acetate | 82(74)[e] | 6.0:1 | 97:3/90:10 |
| 5 | THF | 78 | 5.3:1 | 97:3/92:8 |
| 6 | $CH_2Cl_2$ | 71 | 4.0:1 | 97:3/92:8 |

TABLE S3-continued

Condition optimization for synthesis of γ-lactam 7a from ester 1a and hydrazone 6a

| Entry[a] | Solvent | Yield (%)[b] | d.r.[c] | e.r.[d] |
|---|---|---|---|---|
| 7 | t-BuOH | 74 | 2.4:1 | 96:4/89:11 |
| 8[f] | Ethyl Acetate | 79 | 6.0:1 | 97:3/90:10 |

[a]Reaction was carried out at 0.2M concentration of 6a, with the presence of 200 mg 4Å Molecular Sieve.
[b]Yields were estimated via $^1$H NMR yield.
[c]Diastereomeric ratio, estimated via $^1$H NMR analysis of crude reaction mixture.
[d]Enantiomeric ratio of the 7a and its diastereomer respectively, estimated via chiral phase HPLC analysis.
[e]Isolated yield.
[f]20 mmol % Mg(Ot-Bu)$_2$.

Note:
The corresponding racemic products (for the above three type of reactions) for chiral phase HPLC method development were prepared using similar procedrues in presence of achiral catalyst B or C.

Example 8: Stereochemistry determination (3y & 7j) via X-ray crystillographic analysis. Good quality crystal of 3y (colorless flaky crystal) was obtained by vaporization of a hexane solution of compound 3y. CCDC 900975 contains the supplementary crystallographic data that can be obtained free of charge from The Cambridge Crystallographic Data Centre via www.ccdc.cam.ac.uk/data request/cif.

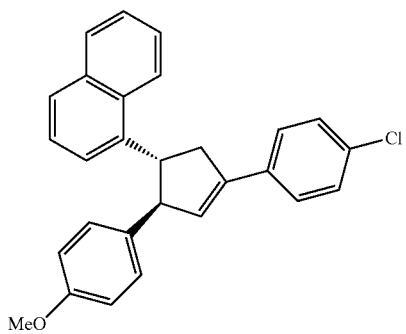

3y

Product 7j was crystallized as a colorless crystal via vaporization of a hexane/ethyl acetate solution, and its absolute configuration was determined by x-ray structure analaysis. CCDC 910100 contains the supplementary crystallographic data that can be obtained free of charge from The Cambridge Crystallographic Data Centre via www.ccdc.cam.ac.uk/data request/cif.

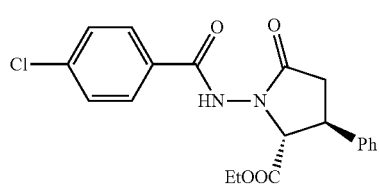

7j

Synthetic Utilities: Transformation of Catalytic Reaction Products to Bioactive Compounds

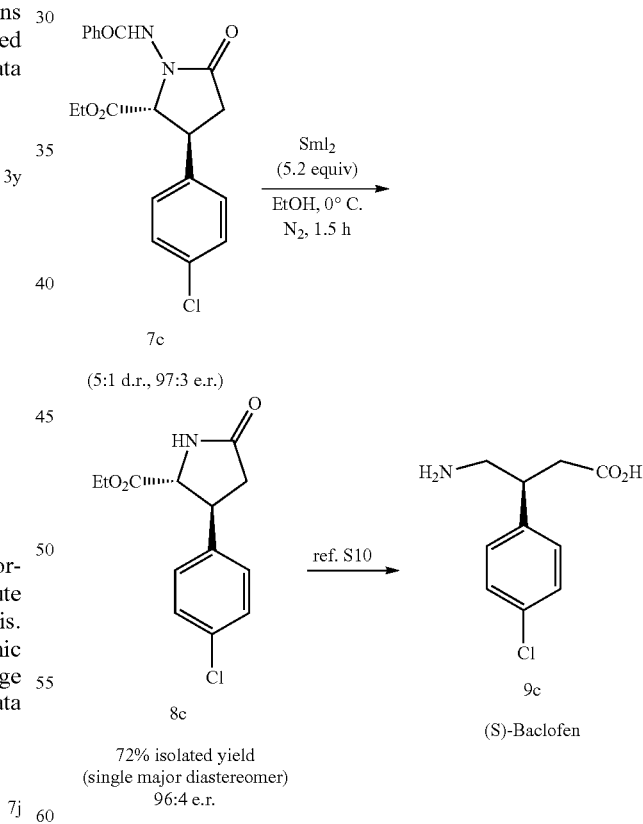

Example 9: Synthesis of (S)-baclefon 9c: A dry 10 mL Schlenk tube equipped with a magnetic stir bar was successively charged with γ-lactam 7c (5:1 d.r., 97:3 e.r., 0.2 mmol). The tube was closed with a septum, evacuated, and refilled with nitrogen. To this mixture was added a 0.1 M solution of SmI$_2$ (5.2 equiv) in THF at 0° C., followed by the addition of EtOH (0.5 mL) via a syringe. After stirring for 1.5 hours at 0° C., the reaction mixture was concentrated under reduced pressure. The crude residue was diluted with ethyl acetate (15 mL) and washed with water. The aqueous layer was extracted with ethyl acetate (2×15 mL) and the combined organic layers were dried over anhydrous sodium sulfate, filtered, and concentrated. The oily residue was applied to silica gel column chromatography (1:100 v/v methanol/DCM) to afford trans γ-lactam 8c as a colorless oil in 72% isolated yield, 96:4 e.r., and cis γ-lactam with 13% isolated yield. Compound 8c can be converted to (S)-Baclofen 9c by adopting a literature procedure.[5]

Example 10: Synthesis of (S)-rolipram 9i: Compound 7i-2 was prepared using a procedure similar to that for the synthesis of 8c above. Compound 7i-2 (50 mg, 0.14 mmol) was dissolved in 5 mL THF and LiBH$_4$ (8 mg, 0.36 mmol) was added in portions. After stirring at room temperature for 4 h, the reaction was quenched with 2 N HCl in an ice bath. The mixture was extracted with ethyl acetate, dried over anhydrous Na$_2$SO$_4$, filtered, and concentrated under reduced pressure. Purification by silicon gel column chromatography gave the product 7i-3 as colorless oil (43 mg, 98% yield).

Compound 7i-3 (30.5 mg, 0.1 mmol) was dissolved in 3 mL anhydrous CH$_2$Cl$_2$, and TBSCI (16.5 mg, 0.11 mmol) and DMAP (14.4 mg, 0.12 mmol) was added. After stirring at room temperature for 3 h, the reaction was quenched with 1N HCl The mixture was extracted with ethyl acetate, dried over anhydrous Na$_2$SO$_4$, and concentrated under reduced pressure. The residue was dissolved in 3 mL anhydrous CH$_2$Cl$_2$, and Boc$_2$O (24.0 mg, 0.11 mmol) and DMAP (14.4 mg, 0.12 mmol) was added. After stirring at room temperature overnight, the reaction was quenched with 1N HCl, extracted with ethyl acetate, dried over anhydrous Na$_2$SO$_4$, and concentrated under reduced pressure. The crude residue was dissolved in 3 mL anhydrous THF and AcOH (6 μL, 0.1 mmol). TBAF (1 M in THF, 0.2 mL, 0.2 mmol) was added. The reaction was stirred at room temperature and monitored by TLC for completion. The mixture was extracted with ethyl acetate, washed with brine and dried over anhydrous Na$_2$SO$_4$, and concentrated under reduced pressure. Purification by column chromatography on silicon gel gave the product 8i as colorless oil (27 mg, 67% yield, 96:4 e.r.).

Compound 8i can be converted to (S)-Rolipram 9i according to literature procedure.[6]

Comparison of Our Ester Reactions with α,β-Unsaturated Aldehyde (Enal) Reactions NHC-catalyzed reactions of ester 1a (OR ENAL 10a) with chalcone 2a (Table S4): The four enantiomers (from two diastereomers) of product 3a and their ratios were assigned via chiral phase HPLC analsyis. The RIS ratios of each chiral center were then calculated. The results summerized in Table S3 showed that reactions with enone 2a of from ester 1a or the corresponding enal 10a gave very different results. Several observations are given below:

TABLE S4

Comparison of enal reactions and our ester β-activation reactions (chalcone as electrophile)

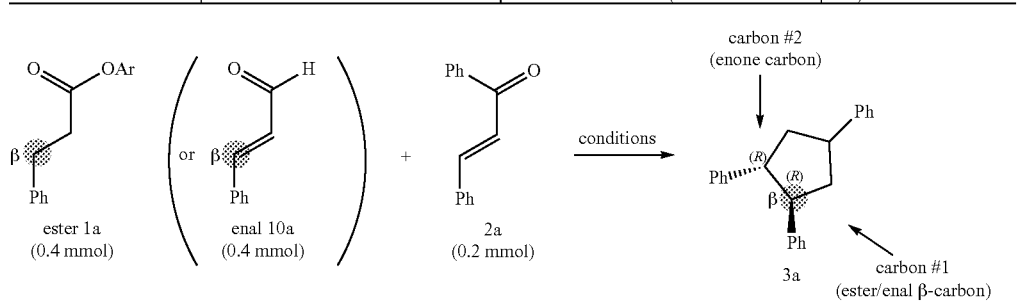

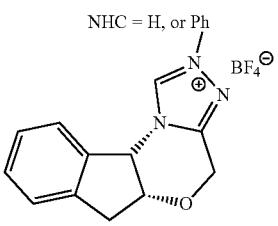

| Entry | Conditions | Reaction | 3a | Carbon #1 (R/S) | Carbon #2 (R/S) |
|---|---|---|---|---|---|
| 1 | 20 mol % H, 150 mol % DBU, CH$_3$CN (as Table 1, entry 9) | ester (1a) | 66% yield, 7:1 d.r. 96:4 e.r.(trans-3a) 81:19 e.r. (cis-3a) | 87:13 | 94:6 |
| 2 | as entry 1 above | enal (10a) | 51% yield, 1.8:1 d.r. 57:43 e.r.(trans-3a) 88:12 e.r. (cis-3a) | 44:56 | 66:34 |
| 3 | as entry 2 above except with 2.3 eq DBU and 2.0 eq 4-NO$_2$PHOH | enal (10a) | 43% yield, 1.2:1 d.r. 57:43 e.r.(trans-3a) 90:10 e.r. (cis-3a) | 41:59 | 68:32 |
| 4 | as entry 1 above except NHC = I | ester (1a) | 25% yield, 16:1 d.r. 85:15 e.r.(trans-3a) 26:74 e.r. (cis-3a) | 84:16 | 81:19 |
| 5 | as entry 4 above | enal (10a) | 24% yield, 1.8:1 d.r. 36:64 e.r.(trans-3a) 92:8e.r. (cis-3a) | 28:72 | 52:48 |

(a) A comparison of entry 1 and 2 showed that the ester reaction gave much better d.r. and e.r. More remarkably, the enal reaction gave 3a with a much lower and even opposite e.r. For example, for carbon #1 of product 3a, the ester reaction (entry 1) favored R-configuration (87:13 R/S), while the enal reaction (entry 2) favored S-configuration (44:56 R/S).

(b) Since the ester reaction (entry 1) released 4-NO2-PhOH in the catalytic reaction; we wondered if the difference in e.r. and d.r was caused by the phenol side product. We therefore added 2.0 equivalents of 4-NO2-PhOH as an additive to the enal reaction (entry 3). To maintain a basic medium for effective reaction, 2.3 eq DBU was also added. A comparison of entry 3 and 2 showed that the additive had only very little influence on the stereo-selectivities. The R/S ratios for each chiral carbon center remained nearly the same (e.g., for carbon #1, 44:56 R/S in entry 2, as compared to 41:59 R/S in entry 3 when phenol additive was introduced).

(c) A comparison of entries 1-3 suggested that that the "similar" homoenolate intermediates obtained using the enal and our ester approaches showed different reactivities and selectivities. More specifically, the enal homoenolate intermediate comes from addition of NHC to the aldehyde group of enal to form a Breslow intermediate. In contrast, our ester "homoenolate" is obtained through β-carbon deprotonation of an "enolate intermediate". The ester "homoenolate" intermediate with a formal nucleophilic β-carbon may be stabilized in a different form. Additional mechanistic studies are in progress.

(d) Similar differences between ester and enal reactions were observed using other conditions and NHC catalysts. For example, with I as an NHC pre-catalyst, the ester and enal reactions gave opposite enantioselectivities for both trans- and cis-3a and both carbon chiral centers of 3a (entries 4-5). Notably, as observed by Bode previously,[7] the enal reaction gave cis-cyclopetene product with high e.r., (e.g., 92:8 e.r., for cis-3a, entry 5), but trans-isomer with low e.r. (e.g., 36:64 e.r. for trans-3a, entry 5). These results again clearly demonstrate the practical utilities of our ester activation strategy in enantioselective synthesis.

Similar Results Were Also Observed When Hydrazone (Table S5) or Trifluoroketone (Table S6) Were Used the Electrophiles:

TABLE S5

Comparison of enal reactions and our ester β-activation reactions (hydrazone as electrophile)

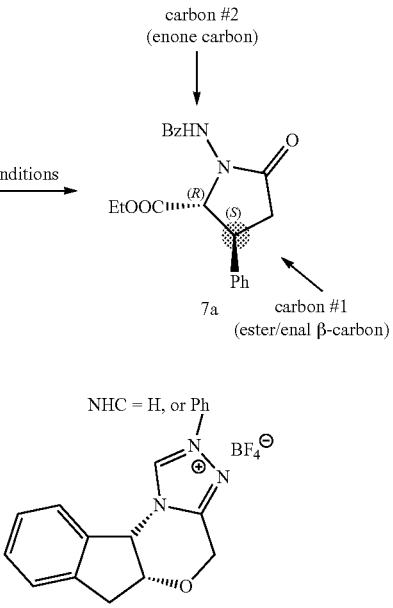

| Entry | Conditions | Reaction | 7a | Carbon #1 (R/S) | Carbon #2 (R/S) |
|---|---|---|---|---|---|
| 1 | 20 mol % H, 150 mol % DBU, EA(0.2 M), 40° C., 48 h | ester (1a) | 74% yield, 6:1 d.r. 97:3 e.r.(trans-7a) 90:10 e.r. (cis-7a) | 13:87 | 97:3 |
| 2 | as entry 1 above | enal (10a) | 20% yield, 1:2.2 d.r. 40:60 e.r.(trans-7a) 3:97 e.r. (cis-7a) | 10:90 | 7:93 |
| 3 | as entry 2 above except with 2.3 eq DBU and 2.0 eq 4-NO₂PHOH | enal (10a) | 20% yield, 1:1.4 d.r. 84:16 e.r.(trans-7a) 11:89 e.r. (cis-7a) | 13:87 | 49:51 |
| 4 | as entry 1 above except NHC = I | ester (1a) | 44% yield, 3.8:1 d.r. 77:23 e.r.(trans-7a) 76:24 e.r. (cis-7a) | 30:70 | 77:23 |
| 5 | as entry 4 above | enal (10a) | 5% yield, nd d.r. 35:65 e.r.(trans-7a) 10:90 e.r. (cis-7a) | 28:72 | 17:83 |

TABLE S6

Comparison of enal reactions and our ester β-activation reactions (trifluoroketone as electrophile)

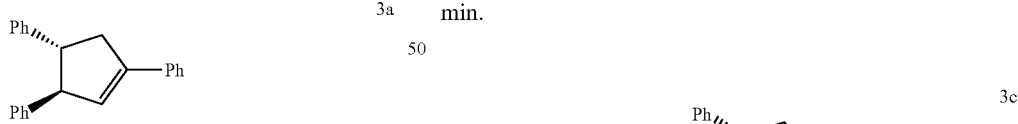

| Entry | Conditions | Reaction | 5a + 5a' | Carbon #1 | Carbon #2 |
|---|---|---|---|---|---|
|  |  |  |  | (R/S) | (R/S) |
| 1 | 20 mol % H, 150 mol % DBU, Tol. (0.2 M), 0° C., 48 h | ester (1a) | 54% yield, 1.3:1 d.r. 91:9 e.r.(5a) 94:6 e.r. (5a') | 8:92 | 46:54 |
| 2 | as entry 1 above | enal (10a) | 38% yield, 1.4:1 d.r. 59:41 e.r.(5a) 80:20 e.r. (5a') | 34:66 | 54:46 |
| 3 | as entry 2 above except with 2.3 eq DBU and 2.0 eq 4-NO$_2$PHOH | enal (10a) | 62% yield, 1:1.1 d.r. 61:39 e.r.(5a) 64:36 e.r. (5a') | 36:64 | 53:47 |
| 4 | as entry 1 above except NHC = I | ester (1a) | 17% yield, 1.2:1 d.r. 65:35 e.r.(5a) 59:41 e.r. (5a') | 38:62 | 49:51 |
| 5 | as entry 4 above | enal (10a) | 19% yield, 1.5:1 d.r. 59:41 e.r.(5a) 49:51 e.r. (5a') | 45:55 | 44:56 |

Characterizations of Products $^1$H NMR and $^{13}$C NMR characterization of exemplary compounds is provided in the following.

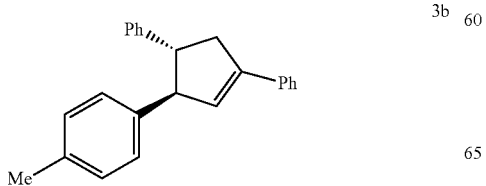

3a

Example 11: (1R,2R)-Cyclopent-3-ene-1,2,4-triyltribenzene: $[\alpha]_D^{23}$ (c 2.23, CH$_2$Cl$_2$)=−138.9°; 95:5 e.r. as determined by HPLC (Chiralcel OD, 99.8:0.2 hexanes/i-PrOH, 0.3 mL/min), t$_r$ (major)=35.8 min, t$_r$ (minor)=46.9 min.

3b

Example 12: ((1R,5R)-5-(p-Tolyl)cyclopent-3-ene-1,3-diyl)dibenzene: $[\alpha]_D^{23}$ (c 1.85, CH$_2$Cl$_2$)=−133.8°; 97:3 e.r. as determined by HPLC (Chiralcel ADH, 99.9:0.1 hexanes/i-PrOH, 0.3 mL/min), t$_r$ (major)=39.1 min, t$_r$ (minor)=51.4 min.

3c

Example 13: ((1R,5R)-5-(4-Methoxyphenyl)cyclopent-3-ene-1,3-diyl)dibenzene: $[\alpha]_D^{23}$ (c 2.83, CH$_2$Cl$_2$)=−116.5°; 95:5 e.r. as determined by HPLC (Chiralcel IA, 99.8:0.2 hexanes/i-PrOH, 0.3 mL/min), t$_r$ (major)=45.4 min, t$_r$ (minor)=41.7 min.

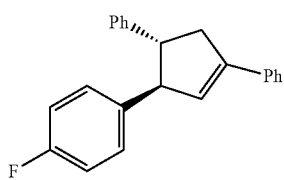
3d

Example 14: ((1R,5R)-5-(4-Fluorophenyl)cyclopent-3-ene-1,3-diyl)dibenzene: $[\alpha]_D^{23}$ (c 1.95, $CH_2Cl_2$)=−110.4°; 96:4 e.r. as determined by HPLC (Chiralcel IA, 99.8:0.2 hexanes/i-PrOH, 0.3 mL/min), $t_r$ (major)=29.1 min, $t_r$ (minor)=23.4 min.

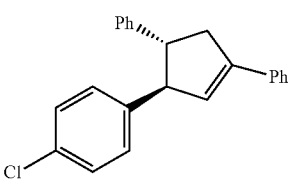
3e

Example 15: ((1R,5R)-5-(4-Chlorophenyl)cyclopent-3-ene-1,3-diyl)dibenzene: $[\alpha]_D^{23}$ (c 2.47, $CH_2Cl_2$)=−117.7°; 95:5 e.r. as determined by HPLC (Chiralcel IA, 99.8:0.2 hexanes/i-PrOH, 0.3 mL/min), $t_r$ (major)=32.0 min, $t_r$ (minor)=25.8 min.

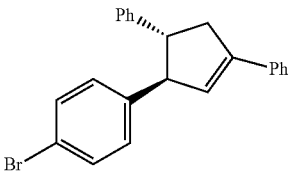
3f

Example 16: ((1R,5R)-5-(4-Bromophenyl)cyclopent-3-ene-1,3-diyl)dibenzene: $[\alpha]_D^{23}$ (c 2.46, $CH_2Cl_2$)=−127.0°; 95:5 e.r. as determined by HPLC (Chiralcel ODH, 99.8:0.2 hexanes/i-PrOH, 0.3 mL/min), $t_r$ (major)=65.2 min, $t_r$ (minor)=97.6 min.

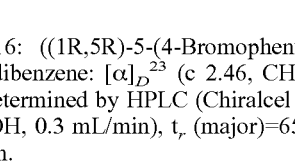
3g

Example 17: 1-((1R,5R)-3,5-Diphenylcyclopent-2-en-1-yl)naphthalene: colorless gum; $[\alpha]_D^{23}$ (c 1.17, $CH_2Cl_2$)=+22.3°; $^1$H NMR (400 MHz, $CDCl_3$) δ=2.98-3.03 (m, 1H), 3.40-3.46 (m, 1H), 3.53-3.57 (m, 1H), 4.89 (dd, J=4.4, 2.0 Hz, 1H), 6.42 (dd, J=4.0, 1.6 Hz, 1H), 6.71-6.75 (m, 1H), 7.23-7.45 (m, 11H), 7.59-7.61 (m, 2H), 7.64-7.79 (m, 2H), 7.85 (d, J=8.0 Hz, 1H); $^{13}$C NMR (100 MHz, $CDCl_3$) δ=147.0, 142.9, 136.0, 134.1, 131.8, 128.7, 128.6, 128.5, 128.5, 128.1, 127.6, 127.1, 127.0, 126.4, 125.9, 125.8, 125.7, 125.6, 125.5, 124.2, 124.0, 56.6, 52.8, 42.0; HRMS (ESI) calcd for $C_{27}H_{23}$ (M+H)$^+$: 347.1800, Found: 347.1797; 95:5 e.r. as determined by HPLC (Chiralcel ODH, 99.8:0.2 hexanes/i-PrOH, 0.3 mL/min), $t_r$ (major)=28.7 min, $t_r$ (minor)=27.4 min.

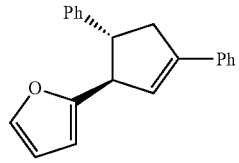
3h

Example 18: 2-((1R,5R)-3,5-Diphenylcyclopent-2-en-1-yl)furan: $[\alpha]_D^{23}$ (c 2.54, $CH_2Cl_2$)=−78.7°; 91:9 e.r. as determined by HPLC (Chiralcel IA, 99.8:0.2 hexanes/i-PrOH, 0.3 mL/min), $t_r$ (major)=28.0 min, $t_r$ (minor)=21.2 min.

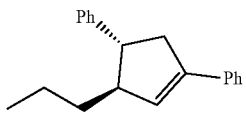
3i

Example 19: ((1R,5R)-5-Propylcyclopent-3-ene-1,3-diyl)dibenzene: $[\alpha]_D^{23}$ (c 0.62, $CH_2Cl_2$)=−24.0°; 91:9 e.r. as determined by HPLC (Chiralcel IA, 99.8:0.2 hexanes/i-PrOH, 0.3 mL/min), $t_r$ (major)=16.0 min, $t_r$ (minor)=13.7 min.

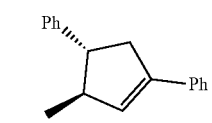
3j

Example 20: ((1R,5R)-5-Methylcyclopent-3-ene-1,3-diyl)dibenzene: colorless gum; $[\alpha]_D^{23}$ (c 0.63, $CH_2Cl_2$)=+48.2°; $^1$H NMR (400 MHz, $CDCl_3$) δ=1.17 (d, J=6.4 Hz, 3H), 2.86-2.93 (m, 1H), 2.98-3.07 (m, 2H), 3.17-3.24 (m, 1H), 6.11-6.12 (m, 1H), 7.20-7.34 (m, 8H), 7.45-7.47 (m, 2H); $^{13}$C NMR (100 MHz, $CDCl_3$) δ=145.8, 140.0, 136.4, 130.8, 128.4, 128.3, 127.5, 127.1, 126.1, 125.6, 53.3, 49.4, 42.2, 19.9; HRMS(ESI) calcd for $C_{18}H_{19}$ (M+H)$^+$: 235.1487, Found: 235.1500; 94:6 e.r. as determined by HPLC (Chiralcel IA, 99.9:0.1 hexanes/i-PrOH, 0.3 mL/min), $t_r$ (major)=15.9 min, $t_r$ (minor)=14.0 min.

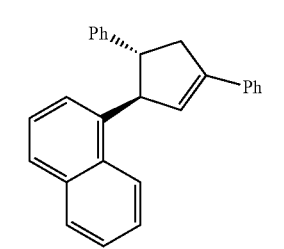
3k

Example 21: Cyclopent-3-ene-1,3-diyldibenzene: colorless gum; $^1$H NMR (400 MHz, $CDCl_3$) δ=2.64-2.69 (m, 1H), 2.83-2.88 (m, 1H), 2.99-3.01 (m, 1H), 3.18 (ddd, J=9.2, 2.4, 1.2 Hz, 1H), 3.62-3.67 (m, 1H), 6.22 (dd, J=4.0, 2.0 Hz, 1H), 7.18-7.34 (m, 8H), 7.47 (dd, J=4.0, 1.2 Hz, 2H); $^{13}$C NMR (100 MHz, $CDCl_3$) b=147.2, 141.5, 136.4, 128.5, 128.4, 127.1, 127.0, 126.0, 125.6, 124.8, 43.5, 42.0, 41.8; HRMS (ESI) calcd for C$_{17}$H$_{17}$ (M+H)$^+$: 221.1330, Found: 221.1342.

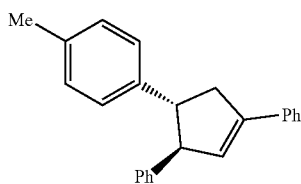

31

Example 22: ((3R,4R)-4-(p-Tolyl)cyclopent-1-ene-1,3-diyl)dibenzene: colorless gum; [α]$_D$$^{23}$ (c 1.13, CH$_2$Cl$_2$)=−147.4°; $^1$H NMR (400 MHz, CDCl$_3$) δ=2.33 (s, 3H), 2.96-3.02 (m, 1H), 3.29-3.44 (m, 2H), 4.09-4.12 (m, 1H), 6.25 (dd, J=3.6, 2.0 Hz, 1H), 7.09-7.38 (m, 12H), 7.52-7.54 (m, 2H); $^{13}$C NMR (100 MHz, CDCl$_3$) δ=145.0, 142.4, 142.2, 136.1, 135.8, 129.2, 128.5, 128.4, 128.2, 127.5, 127.4, 127.2, 126.4, 125.8, 60.8, 54.2, 42.1, 21.1; HRMS(ESI) calcd for C$_{24}$H$_{23}$ (M+H)$^+$: 311.1800, Found: 311.1798; 95:5 e.r. as determined by HPLC (Chiralcel OD, 99.8:0.2 hexanes/i-PrOH, 0.3 mL/min), t$_r$ (major)=29.9 min, t$_r$ (minor)=37.9 min.

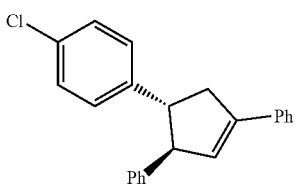

3m

Example 23: ((3R,4R)-4-(4-Chlorophenyl)cyclopent-1-ene-1,3-diyl)dibenzene: colorless gum; [α]$_D$$^{23}$ (c 1.27, CH$_2$Cl$_2$)=−116.3°; $^1$H NMR (400 MHz, CDCl$_3$) δ=2.93-2.99 (m, 1H), 3.29-3.42 (m, 2H), 4.05-4.07 (m, 1H), 6.24 (dd, J=3.6, 2.0 Hz, 1H), 7.11-7.39 (m, 12H), 7.51-7.54 (m, 2H); $^{13}$C NMR (100 MHz, CDCl$_3$) δ=144.5, 143.8, 142.1, 135.8, 132.0, 128.7, 128.6, 128.6, 128.5, 128.0, 127.7, 127.4, 126.6, 125.8, 60.9, 54.0, 41.9; HRMS(ESI) calcd for C$_{23}$H$_{19}$Cl (M+Na)$^+$: 353.1073, Found: 353.1060; 95:5 e.r. as determined by HPLC (Chiralcel IA, 99.8:0.2 hexanes/i-PrOH, 0.3 mL/min), t$_r$ (major)=31.8 min, t$_r$ (minor)=25.1 min.

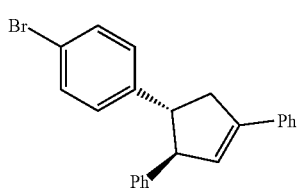

3n

Example 24: ((3R,4R)-4-(4-Bromophenyl)cyclopent-1-ene-1,3-diyl)dibenzene: colorless gum; [α]$_D$$^{23}$ (c 2.42, CH$_2$Cl$_2$)=−117.1°; $^1$H NMR (400 MHz, CDCl$_3$) δ=2.96 (dd, J=15.2, 7.2 Hz, 1H), 3.32-3.41 (m, 2H), 4.05-4.07 (m, 1H), 6.24 (dd, J=3.6, 2.0 Hz, 1H), 7.10-7.42 (m, 12H), 7.52-7.54 (m, 2H); $^{13}$C NMR (100 MHz, CDCl$_3$) δ=144.5, 144.4, 142.1, 135.8, 131.6, 129.1, 128.6, 128.5, 128.0, 127.7, 127.4, 126.6, 125.8, 120.0, 60.9, 54.1, 41.8; HRMS(ESI) calcd for C$_{23}$H$_{20}$Br (M+H)$^+$: 375.0748, Found: 375.0728; 95:5 e.r. as determined by HPLC (Chiralcel IA, 99.9:0.1 hexanes/i-PrOH, 0.3 mL/min), t$_r$ (major)=37.4 min, t$_r$ (minor)=27.6 min.

3o

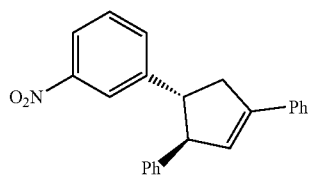

Example 25: ((3R,4R)-4-(4-Nitrophenyl)cyclopent-1-ene-1,3-diyl)dibenzene: colorless gum; [α]$_D$$^{23}$ (c 1.61, CH$_2$Cl$_2$)=−104.4°; $^1$H NMR (400 MHz, CDCl$_3$) δ=3.02 (dd, J=16.0, 7.2 Hz, 1H), 3.37-3.44 (m, 1H), 3.53-3.57 (m, 1H), 4.10-4.12 (m, 1H), 6.27 (dd, J=3.6, 2.0 Hz, 1H), 7.11-7.13 (m, 2H), 7.24-7.42 (m, 8H), 7.53-7.55 (m, 2H), 8.13-8.17 (m, 2H); $^{13}$C NMR (100 MHz, CDCl$_3$) δ=153.2, 146.7, 144.0, 142.1, 135.5, 128.7, 128.6, 128.2, 127.9, 127.8, 127.4, 126.9, 125.9, 123.9, 70.0, 54.4, 41.7; HRMS(ESI) calcd for C$_{23}$H$_{20}$NO$_2$ (M+H)$^+$: 342.1494, Found: 342.1500; 95:5 e.r. as determined by HPLC (Chiralcel IA, 99:1 hexanes/i-PrOH, 0.3 mL/min), t$_r$ (major)=86.5 min, t$_r$ (minor)=46.4 min.

3p

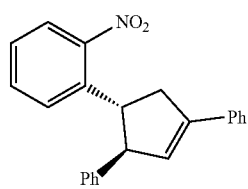

Example 26: ((3R,4R)-4-(3-Nitrophenyl)cyclopent-1-ene-1,3-diyl)dibenzene: colorless gum; [α]$_D$$^{23}$ (c 1.03, CH$_2$Cl$_2$)=−53.4°; $^1$H NMR (400 MHz, CDCl$_3$) δ=2.98-3.04 (m, 1H), 3.37-3.43 (m, 1H), 3.53-3.59 (m, 1H), 4.11-4.14 (m, 1H), 6.26 (d, J=1.2 Hz, 1H), 7.12-7.45 (m, 9H), 7.53 (d, J=7.6 Hz, 3H), 8.06-8.09 (m, 1H), 8.14 (d, J=2.0 Hz, 1H); $^{13}$C NMR (100 MHz, CDCl$_3$) δ=148.5, 147.4, 144.0, 142.0, 135.5, 133.8, 129.5, 128.8, 128.7, 128.6, 127.9, 127.4, 126.9, 125.9, 122.2, 121.6, 60.8, 54.2, 41.8; HRMS(ESI) calcd for C$_{23}$H$_{19}$NO$_2$Na (M+Na)$^+$: 364.1313, Found: 364.1298; 96:4 e.r. as determined by HPLC (Chiralcel ADH, 99:1 hexanes/i-PrOH, 0.3 mL/min), t$_r$ (major)=72.1 min, t$_r$ (minor)=48.4 min.

3q

Example 27: ((3R,4R)-4-(2-Nitrophenyl)cyclopent-1-ene-1,3-diyl)dibenzene: colorless gum; [α]$_D$$^{23}$ (c 1.0, CH$_2$Cl$_2$)=−55.0°; $^1$H NMR (400 MHz, CDCl$_3$) δ=2.89-2.95

(m, 1H), 3.50-3.56 (m, 1H), 3.89-3.95 (m, 1H), 4.22 (dd, J=5.6, 2.4 Hz, 1H), 6.30 (d, J=2.0 Hz, 1H), 7.11-7.39 (m, 9H), 7.52-7.57 (m, 3H), 7.65-7.69 (m, 2H); $^{13}$C NMR (100 MHz, CDCl$_3$) δ=150.1, 143.8, 142.1, 140.1, 135.5, 132.8, 128.7, 128.6, 128.5, 128.0, 127.9, 127.3, 127.1, 126.9, 125.9, 123.8, 60.4, 47.7, 42.4; HRMS(ESI) calcd for C$_{23}$H$_{19}$NO$_2$Na (M+Na)$^+$: 364.1313, Found: 364.1318; 96:4 e.r. as determined by HPLC (Chiralcel IA, 99.9:0.1 hexanes/i-PrOH, 0.3 mL/min), t$_r$ (major)=63.8 min, t$_r$ (minor)=56.3 min.

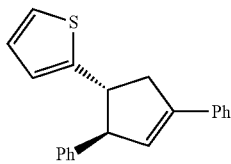

3r

Example 28: 2-((1R,2R)-2,4-Diphenylcyclopent-3-en-1-yl)thiophene: [α]$_D^{23}$ (c 2.56, CH$_2$Cl$_2$)=−70.8°; 94:6 e.r. as determined by HPLC (Chiralcel IA, 99.8:0.2 hexanes/i-PrOH, 0.3 mL/min), t$_r$ (major)=29.0 min, t$_r$ (minor)=25.5 min.

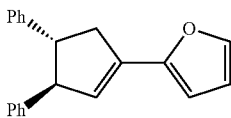

3s

Example 29: 2-((3R,4R)-3,4-Diphenylcyclopent-1-en-1-yl)furan: [α]$_D^{23}$ (c 1.66, CH$_2$Cl$_2$)=−127.4°; 94:6 e.r. as determined by HPLC (Chiralcel OD, 99.8:0.2 hexanes/i-PrOH, 0.3 mL/min), t$_r$ (major)=34.4 min, t$_r$ (minor)=49.9 min.

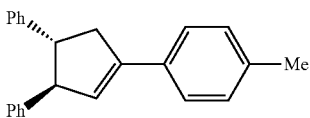

3t

Example 30: ((1R,2R)-4-(p-Tolyl)cyclopent-3-ene-1,2-diyl)dibenzene: colorless gum; [α]$_D^{23}$ (c 1.00, CH$_2$Cl$_2$)=−112.4°; $^1$H NMR (400 MHz, CDCl$_3$) δ=2.37 (s, 3H), 2.96-3.02 (m, 1H), 3.29-3.46 (m, 2H), 4.10-4.13 (m, 1H), 6.20 (t, J=1.6 Hz, 1H), 7.13-7.31 (m, 12H), 7.42-7.49 (m, 2H); $^{13}$C NMR (100 MHz, CDCl$_3$) δ=145.6, 145.1, 142.1, 137.4, 133.2, 129.2, 128.5, 128.4, 127.5, 127.3, 127.1, 126.4, 126.3, 125.7, 60.8, 54.5, 42.0, 21.3; HRMS(ESI) calcd for C$_{24}$1-H$_{23}$ (M+H)$^+$: 311.1800, Found: 311.1804; 95:5 e.r. as determined by HPLC (Chiralcel IA, 99.8:0.2 hexanes/i-PrOH, 0.3 mL/min), t$_r$ (major)=26.1 min, t$_r$ (minor)=24.2 min.

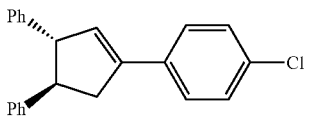

3u

Example 31: ((1R,2R)-4-(4-Chlorophenyl)cyclopent-3-ene-1,2-diyl)dibenzene: colorless gum; [α]$_D^{23}$ (c 2.14, CH$_2$Cl$_2$)=−89.5°; $^1$H NMR (400 MHz, CDCl$_3$) δ=2.94-3.01 (m, 1H), 3.26-3.34 (m, 1H), 3.42-3.48 (m, 1H), 4.11-4.14 (m, 1H), 6.24 (dd, J=3.6, 2.0 Hz, 1H), 7.12-7.34 (m, 12H), 7.43-7.46 (m, 2H); $^{13}$C NMR (100 MHz, CDCl$_3$) δ=145.1, 144.6, 141.1, 134.5, 133.2, 128.9, 128.6, 128.5, 128.5, 127.4, 127.3, 127.1, 126.5, 126.4, 60.8, 54.5, 42.0; HRMS (ESI) calcd for C$_{23}$H$_{20}$Cl (M+H)$^+$: 331.1254, Found: 331.1277; 95:5 e.r. as determined by HPLC (Chiralcel IA, 99.8:0.2 hexanes/i-PrOH, 0.3 mL/min), t$_r$ (major)=31.4 min, t$_r$ (minor)=29.3 min.

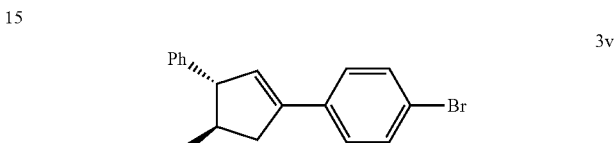

3v

Example 32: ((1R,2R)-4-(4-Bromophenyl)cyclopent-3-ene-1,2-diyl)dibenzene: [α]$_D^{23}$ (c 2.78, CH$_2$Cl$_2$)=−87.5°; 96:4 e.r. (1R, 2R)-isomer as determined by HPLC (Chiralcel IA, 99.9:0.1 hexanes/i-PrOH, 0.3 mL/min), t$_r$ (major)=35.2 min, t$_r$ (minor)=32.4 min.

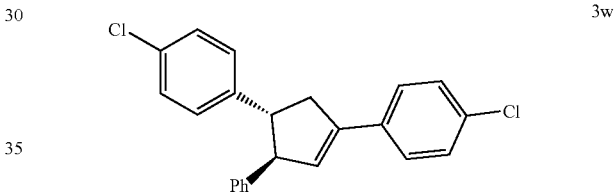

3w

Example 33: 4,4'-((1R,5R)-5-Phenylcyclopent-3-ene-1,3-diyl)bis(chlorobenzene): [α]$_D^{23}$ (c 2.5, CH$_2$Cl$_2$)=−94.4°; 95:5 e.r. isomer as determined by HPLC (Chiralcel IA, 99.8:0.2 hexanes/i-PrOH, 0.3 mL/min), t$_r$ (major)=49.5 min, t$_r$ (minor)=38.1 min.

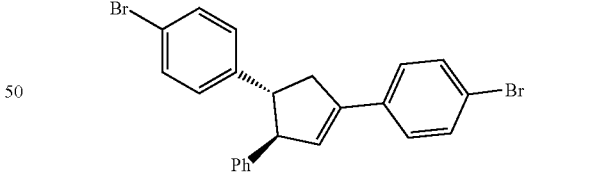

3x

Example 34: 4,4'-((1R,5R)-5-Phenylcyclopent-3-ene-1,3-diyl)bis(bromobenzene): colorless gum; [α]$_D^{23}$ (c 3.45, CH$_2$Cl$_2$)=−68.8°; $^1$H NMR (400 MHz, CDCl$_3$) δ=2.89-2.96 (m, 1H), 3.25-3.27 (m, 1H), 3.30-3.43 (m, 1H), 4.03-4.05 (m, 1H), 6.23 (d, J=1.6 Hz, 1H), 7.08-7.49 (m, 13H); $^{13}$C NMR (100 MHz, CDCl$_3$) δ=144.2, 144.0, 141.1, 134.7, 131.7, 131.6, 130.7, 129.1, 128.9, 128.6, 127.4, 126.7, 121.5, 120.1, 60.9, 54.1, 41.8; HRMS(ESI) calcd for C$_{23}$H$_{19}$Br$_2$ (M+H)$^+$: 452.9854, Found: 452.9868; 95:5 e.r. as determined by HPLC (Chiralcel IA, 99.8:0.2 hexanes/i-PrOH, 0.3 mL/min), t$_r$ (major)=59.2 min, t$_r$ (minor)=46.3 min.

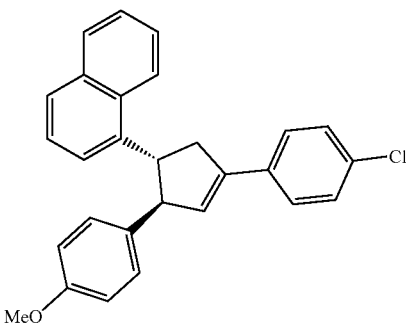

Example 35: 1-((1R,2R)-4-(4-Chlorophenyl)-2-(4-methoxyphenyl)cyclopent-3-en-1-yl)naphthalene: $[\alpha]_D^{23}$ (c 3.0, $CH_2Cl_2$)=−124.4°; 97:3 e.r. as determined by HPLC (Chiralcel OD, 98:2 hexanes/i-PrOH, 0.3 mL/min), $t_r$ (major)=59.8 min, $t_r$ (minor)=38.4 min.

Note: For the products characterized as below, the two diastereomers (e.g., 5a and 5a') were isolated as a mixture.

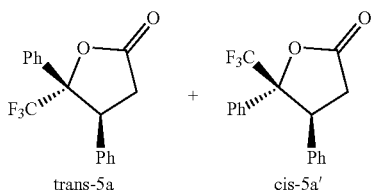 [SMILES: O=C1C[C@@H](c2ccccc2)[C@](c2ccccc2)(C(F)(F)F)O1 ; O=C1C[C@@H](c2ccccc2)[C@@](c2ccccc2)(C(F)(F)F)O1]

Example 36: 4,5-Diphenyl-5-(trifluoromethyl)dihydrofuran-2(3H)-one: 91:9 e.r. (5a), 94:6 e.r. (5a') as determined by HPLC (Chiralcel OD, 99:1 hexanes/i-PrOH, 0.7 mL/min), $t_r$ (5a-major)=23.1 min, $t_r$ (5a-minor)=44.0 min, $t_r$ (5a'-major)=19.8 min, $t_r$ (5a'-minor)=71.3 min.

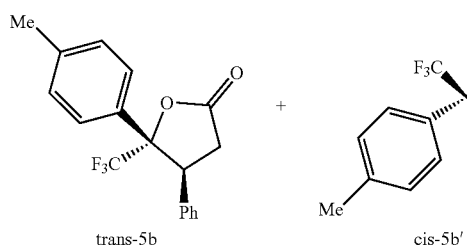

Example 37: 4-phenyl-5-(p-tolyl)-5-(trifluoromethyl)dihydrofuran-2(3H)-one: 93:7 e.r. (5b), 95:5 e.r. (5b') as determined by HPLC (Chiralcel OD, 99.8:0.2 hexanes/i-PrOH, 0.7 mL/min), $t_r$ (5b-major)=30.5 min, $t_r$ (5b-minor)=81.3 min, $t_r$ (5b'-major)=34.5 min, $t_r$ (5b'-minor)=106.5 min.

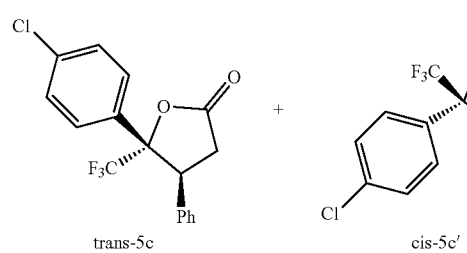

Example 38: 5-(4-chlorophenyl)-4-phenyl-5-(trifluoromethyl)dihydrofuran-2(3H)-one: 94:6 e.r. (5c), 94:6 e.r. (5c') as determined by HPLC (Chiralcel IA, 99:1 hexanes/i-PrOH, 0.7 mL/min), $t_r$ (5c-major)=18.2 min, $t_r$ (5c-minor)=38.5 min, $t_r$ (5c'-major)=19.4 min, $t_r$ (5c'-minor)=69.2 min.

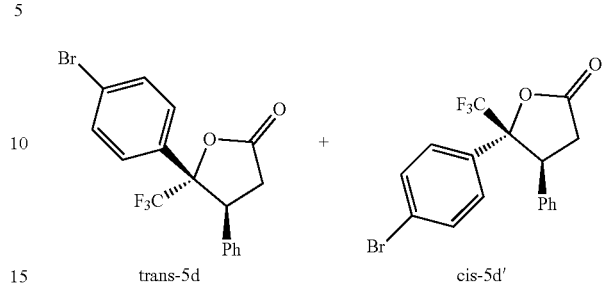

Example 39: 5-(4-bromophenyl)-4-phenyl-5-(trifluoromethyl)dihydrofuran-2(3H)-one: colorless oil; $^1$H NMR (400 MHz, $CDCl_3$) δ=2.74-2.81 (trans, m, 1H), 2.95-2.97 (cis, m, 1H), 3.17-3.32 (cis, m, 1H), 3.34-3.39 (trans, m, 1H), 3.93 (cis, t, J=9.6 Hz, 1H), 4.26 (trans, dd, J=9.6, 5.2 Hz, 1H), 6.84-6.87 (trans, m, 2H), 7.01 (trans, d, J=8.4 Hz, 2H), 7.13-7.16 (trans, m, 3H), 7.27-7.33 (trans+cis, m, 4H), 7.39-7.42 (cis, m, 5H), 7.56-7.58 (cis, m, 2H); $^{13}$C NMR (100 MHz, $CDCl_3$) δ=173.4 (trans), 172.7 (cis), 137.4 (trans), 134.5, 133.2, 132.0, 131.1, 130.5, 129.3, 129.0, 128.9, 128.9, 128.8, 128.7, 128.3, 128.1, 127.3, 127.3, 125.7, 124.1, 123.4, 122.9, 88.2 (q, J=290 Hz) (trans), 87.3 (q, J=260 Hz) (cis), 51.6 (cis), 45.7 (trans), 36.8 (trans), 35.1 (cis); HRMS (ESI) calcd for $C_{17}H_{13}O_2F_3Br$ (M+H)$^+$: 385.0051, Found: 385.0055; 93:7 e.r. (5d), 94:6 e.r. (5d') as determined by HPLC (Chiralcel IB, 98:2 hexanes/i-PrOH, 0.5 mL/min), $t_r$ (5d-major)=22.1 min, $t_r$ (5d-minor)=44.7 min, $t_r$ (5d'-major)=24.3 min, $t_r$ (5d'-minor)=74.6 min.

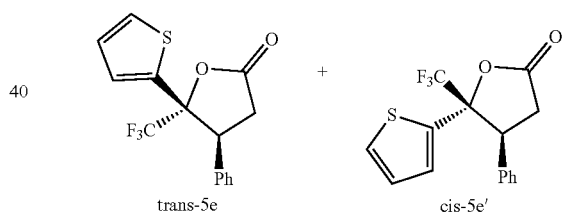

Example 40: 4-phenyl-5-(thiophen-2-yl)-5-(trifluoromethyl)dihydrofuran-2(3H)-one: 90:10 e.r. (5e), 91:9 e.r. (5e') as determined by HPLC (Chiralcel OD, 99:1 hexanes/i-PrOH, 0.7 mL/min), $t_r$ (5e-major)=41.6 min, $t_r$ (5e-minor)=70.5 min, $t_r$ (5e'-major)=26.6 min, $t_r$ (5e'-minor)=87.1 min.

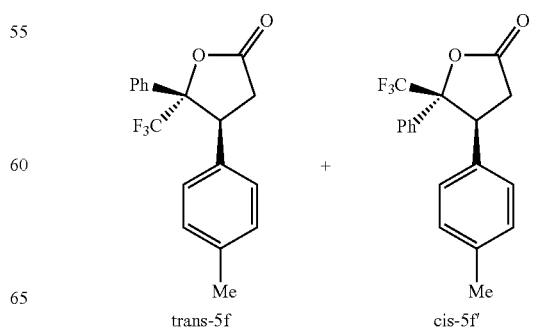

Example 41: 5-phenyl-4-(p-tolyl)-5-(trifluoromethyl)dihydrofuran-2(3H)-one: colorless oil; $^1$H NMR (400 MHz, CDCl$_3$) δ=2.21 (trans, s, 3H), 2.39 (cis, s, 3H), 2.71-2.77 (trans, m, 1H), 2.90 (cis, q, J=8.8 Hz, 1H), 3.14 (cis, dd, J=18.0, 10.0 Hz, 1H), 3.26-3.33 (trans, m, 1H), 3.97 (cis, t, J=5.2 Hz, 1H), 4.25 (trans, dd, J=9.2, 5.6 Hz, 1H), 6.71 (trans, d, J=8.0 Hz, 2H), 6.91 (trans, d, J=8.0 Hz, 2H), 7.12-7.22 (trans+cis, m, 10H), 7.44 (trans, dd, J=6.4, 3.6 Hz, 2H), 7.53-7.54 (cis, m, 2H); $^{13}$C NMR (100 MHz, CDCl$_3$) δ=173.9 (trans), 173.4 (cis), 138.6 (cis), 137.6 (trans), 135.6 (cis), 134.4 (trans), 131.3 (trans), 130.7 (cis), 129.5, 129.4, 129.2, 128.8, 128.7, 128.3, 127.8, 127.0, 126.9, 126.0, 125.6, 125.3, 123.2, 122.5, 88.5 (q, J=280 Hz) (trans), 87.4 (q, J=280 Hz) (cis), 51.2 (cis), 45.5 (trans), 36.8 (trans), 35.3 (cis), 21.1 (cis), 21.0 (trans); HRMS(ESI) calcd for C$_{18}$H$_{16}$O$_2$F$_3$ (M+H)$^+$: 321.1102, Found: 321.1101; 92:8 e.r. (5f), 95:5 e.r. (5f') as determined by HPLC (Chiralcel OD, 95:5 hexanes/i-PrOH, 0.7 mL/min), t$_r$ (5f-major)=19.5 min, t$_r$ (5f-minor)=34.7 min, t$_r$ (5f'-major)=14.8 min, t$_r$ (5f'-minor)=40.3 min.

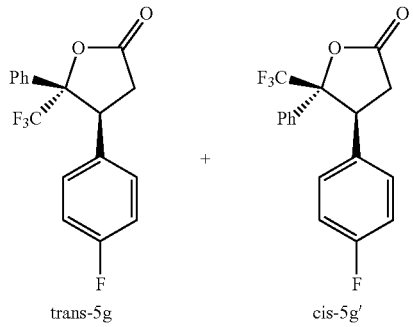 [SMILES: O=C1C[C@@H](c2ccc(F)cc2)[C@](c2ccccc2)(C(F)(F)F)O1 ; O=C1C[C@@H](c2ccc(F)cc2)[C@@](c2ccccc2)(C(F)(F)F)O1]

trans-5g     cis-5g'

Example 42: 4-(4-fluorophenyl)-5-phenyl-5-(trifluoromethyl)dihydrofuran-2(3H)-one: colorless oil; $^1$H NMR (400 MHz, CDCl$_3$) δ=2.70-2.76 (m, 1H), 3.29-3.37 (m, 1H), 4.28 (dd, J=9.6, 5.6 Hz, 1H), 4.03-4.05 (m, 1H), 6.80 (d, J=6.8 Hz, 4H), 7.11-7.22 (m, 5H); $^{13}$C NMR (100 MHz, CDCl$_3$) δ=173.5, 163.3, 160.8, 133.4, 133.3, 131.1, 130.1, 130.0, 129.0, 128.0, 126.8, 115.6, 115.4, 88.4 (q, J=290 Hz), 45.2, 36.8; HRMS(ESI) calcd for C$_{17}$H$_{13}$O$_2$F$_4$ (M+H)$^+$: 325.0852, Found: 325.0852; 95:5 e.r. (5g), 92:8 e.r. (5g') as determined by HPLC (Chiralcel OD, 99:1 hexanes/i-PrOH, 0.7 mL/min), t$_r$ (5g-major)=28.5 min, t$_r$ (5g-minor)=26.1 min, t$_r$ (5g'-major)=23.1 min, t$_r$ (5g'-minor)=39.8 min.

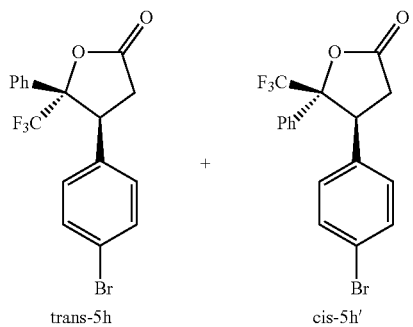 [SMILES: O=C1C[C@@H](c2ccc(Br)cc2)[C@](c2ccccc2)(C(F)(F)F)O1 ; O=C1C[C@@H](c2ccc(Br)cc2)[C@@](c2ccccc2)(C(F)(F)F)O1]

trans-5h     cis-5h'

Example 43: 4-(4-bromophenyl)-5-phenyl-5-(trifluoromethyl)dihydrofuran-2(3H)-one: colorless oil; $^1$H NMR (400 MHz, CDCl$_3$) δ=2.67-2.74 (trans, m, 1H), 2.93-2.96 (cis, m, 1H), 3.06-3.09 (cis, m, 1H), 3.29-3.67 (trans, m, 1H), 3.97 (cis, t, J=9.2 Hz, 1H), 4.25 (trans, dd, J=9.6, 5.2 Hz, 1H), 6.71 (trans, d, J=8.8 Hz, 2H), 7.12-7.26 (trans+cis, m, 10H), 7.44-7.46 (trans, m, 2H), 7.50-7.56 (cis, m, 4H); $^{13}$C NMR (100 MHz, CDCl$_3$) δ=173.3 (trans), 172.8 (cis), 136.7 (trans), 135.2 (cis), 133.0, 132.0, 131.7, 131.0, 130.9, 130.0, 129.7, 129.2, 128.9, 128.1, 126.8, 126.8, 125.9, 125.5, 123.0, 122.9, 121.9, 88.9 (q, J=280 Hz) (trans), 87.6 (q, J=280 Hz) (cis), 51.0 (cis), 45.4 (trans), 36.7 (trans), 35.1 (cis); HRMS(ESI) calcd for C$_{17}$H$_{12}$O$_2$F$_3$BrNa (M+Na)$^+$: 406.9870, Found: 406.9860; 94:6 e.r. (5h), 96:4 e.r. (5h') as determined by HPLC (Chiralcel OD, 99:1 hexanes/i-PrOH, 0.7 mL/min), t$_r$ (5h-major)=52.9 min, t$_r$ (5h-minor)=114.9 min, t$_r$ (5h'-major)=41.4 min, t$_r$ (5h'-minor)=130.2 min.

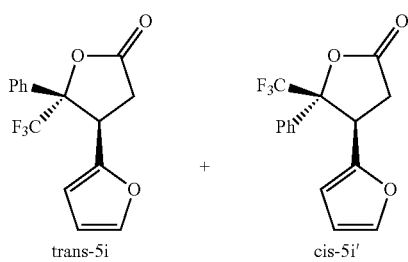 [SMILES: O=C1C[C@@H](c2ccco2)[C@](c2ccccc2)(C(F)(F)F)O1 ; O=C1C[C@@H](c2ccco2)[C@@](c2ccccc2)(C(F)(F)F)O1]

trans-5i     cis-5i'

Example 44: 4-(furan-2-yl)-5-phenyl-5-(trifluoromethyl)dihydrofuran-2(3H)-one: 84:16 e.r. (5i), 84:16 e.r. (5i') as determined by HPLC (Chiralcel OJ-H, 95:5 hexanes/i-PrOH, 0.5 mL/min), t$_r$ (5i-major)=18.9 min, t$_r$ (5i-minor)=28.9 min, t$_r$ (5i'-major)=74.1 min, t$_r$ (5i'-minor)=62.6 min.

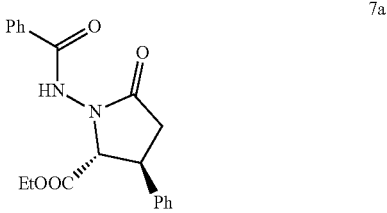 [SMILES: CCOC(=O)[C@H]1[C@H](c2ccccc2)CC(=O)N1NC(=O)c1ccccc1]

7a

Example 45: (2R,3R)-ethyl 1-benzamido-5-oxo-3-phenylpyrrolidine-2-carboxylate: colorless oil; [α]$_D^{23}$ (c 0.94, CH$_2$Cl$_2$)=−39.1°. $^1$H NMR (400 MHz, CDCl$_3$) δ 0.81 (t, J=7.2 Hz, 3H), 2.92 (d, J=8.8 Hz, 2H), 3.64-3.72 (m, 1H), 3.77-3.85 (m, 1H), 4.10-4.17 (m, 1H), 4.96 (d, J=8.8 Hz, 1H), 7.25-7.36 (m, 5H), 7.45 (t, J=8.0 Hz, 2H), 7.56 (t, J=7.6 Hz, 1H), 7.83 (d, J=8.0 Hz, 2H), 8.29 (s, 1H). HRMS(ESI) calcd for C$_{20}$H$_{20}$N$_2$O$_4$ (M+H)$^+$: 353.1501, Found: 353.1496; 97:3 e.r. as determined by HPLC [Chiralcel IA, 75:20:5 hexanes/(hexanes:i-PrOH:CH$_3$OH=90:5:5)/i-PrOH, 0.7 mL/min)], t$_r$ (major)=110.2 min, t$_r$ (minor)=88.3 min.

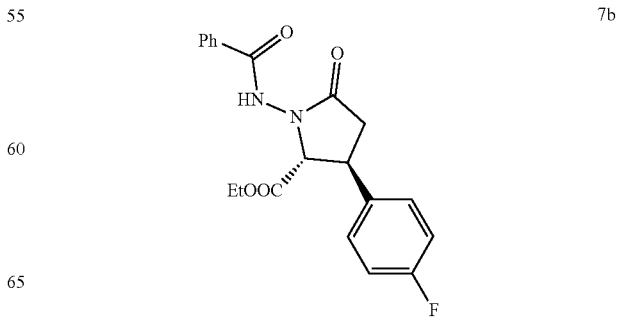

7b

Example 46: (2R,3S)-ethyl1-benzamido-3-(4-fluorophenyl)-5-oxopyrrolidine-2-carboxylate: yellow oil; $[\alpha]_D^{23}$ (c 1.95, $CH_2Cl_2$)=−44.9°; $^1$H NMR (400 MHz, $CDCl_3$) δ=1.23 (t, J=7.2 Hz, 3H), 2.63 (dd, J=17.6 Hz, 9.6 Hz, 1H), 3.04 (dd, J=17.6 Hz, 9.6 Hz, 1H), 3.56-3.61 (m, 1H), 4.17-4.29 (m, 2H), 4.68 (d, J=5.2 Hz, 1H), 7.09 (t, J=8.4 Hz, 2H), 7.41-7.49 (m, 4H), 7.55 (t, J=7.2 Hz, 1H), 7.85 (d, J=7.2 Hz, 2H), 8.61 (bs, 1H); $^{13}$C NMR (100 MHz, $CDCl_3$) δ=172.5, 170.8, 166.1, 163.5, 161.0, 137.3 (d, J=3.0 Hz), 132.7, 131.2, 128.9 (d, J=9.0 Hz), 128.7, 127.5, 116.0 (d, J=21.0 Hz), 67.3, 62.0, 39.9, 36.8, 14.1; HRMS(ESI) calcd for $C_{20}H_{20}N_2O_4F$ (M+H)$^+$: 371.1407, Found: 371.1410; 97:3 e.r. as determined by HPLC [Chiralcel IA, 75:20:5 hexanes/(hexanes:i-PrOH:$CH_3OH$=90:5:5)/i-PrOH, 0.7 mL/min)], $t_r$ (major)=127.3 min, $t_r$ (minor)=105.4 min.

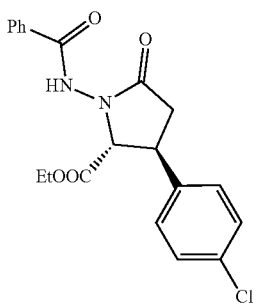

7c

Example 47: (2R,3S)-ethyl1-benzamido-3-(4-chlorophenyl)-5-oxopyrrolidine-2-carboxylate: yellow oil; $[\alpha]_D^{23}$ (c 1.89, $CH_2Cl_2$)=−67.2°; $^1$H NMR (400 MHz, $CDCl_3$) δ=1.23 (t, J=7.2 Hz, 3H), 2.64 (dd, J=17.6 Hz, 6.4 Hz, 1H), 3.06 (dd, J=17.6 Hz, 9.6 Hz, 1H), 3.56-3.61 (m, 1H), 4.15-4.30 (m, 2H), 4.67 (d, J=5.6 Hz, 1H), 7.37-7.45 (m, 6H), 7.52 (t, J=7.6 Hz, 1H), 7.84 (d, J=7.2 Hz, 2H), 8.83 (bs, 1H); $^{13}$C NMR (100 MHz, $CDCl_3$) δ=172.7, 170.7, 166.1, 140.0, 133.6, 132.6, 131.1, 129.3, 128.7, 128.6, 127.6, 67.1, 62.0, 40.0, 36.7, 14.1; HRMS(ESI) calcd for $C_{20}H_{20}N_2O_4Cl$ (M+H)$^+$: 387.1112, Found: 387.1112; 97:3 e.r. as determined by HPLC [Chiralcel IA, 75:20:5 hexanes/(hexanes:i-PrOH:$CH_3OH$=90:5:5)/i-PrOH, 0.7 mL/min)], $t_r$ (major)=136.0 min, $t_r$ (minor)=112.0 min.

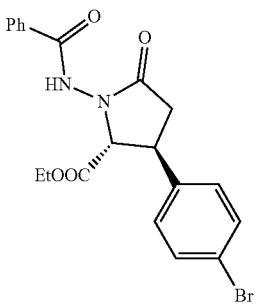

7d

Example 48: (2R,3S)-ethyl1-benzamido-3-(4-bromophenyl)-5-oxopyrrolidine-2-carboxylate: yellow oil; $[\alpha]_D^{23}$ (c 2.49, $CH_2Cl_2$)=−61.8°; $^1$H NMR (400 MHz, $CDCl_3$) δ=1.21 (t, J=7.2 Hz, 3H), 2.64 (dd, J=17.6 Hz, 6.4 Hz, 1H), 3.11 (dd, J=17.6 Hz, 9.6 Hz, 1H), 3.56-3.61 (m, 1H), 4.15-4.26 (m, 2H), 4.68 (d, J=5.6 Hz, 1H), 7.34-7.54 (m, 7H), 7.84 (d, J=7.2 Hz, 2H), 9.49 (bs, 1H); $^{13}$C NMR (100 MHz, $CDCl_3$) δ=173.4, 170.7, 166.0, 140.4, 132.5, 132.2, 130.9, 129.0, 128.6, 127.6, 121.7, 67.1, 62.0, 40.1, 36.8, 14.1; HRMS (ESI) calcd for $C_{20}H_{20}N_2O_4Br^+$: 431.0606, Found: 431.0606; 97:3 e.r. as determined by HPLC [Chiralcel IA, 75:20:5 hexanes/(hexanes:i-PrOH:$CH_3OH$=90:5:5)/i-PrOH, 0.7 mL/min)], $t_r$ (major)=142.7 min, $t_r$ (minor)=118.4 min.

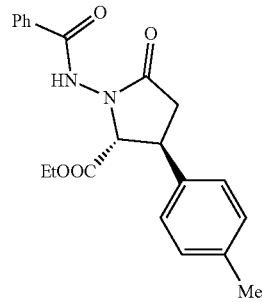

7e

Example 49: (2R,3S)-ethyl 1-benzamido-5-oxo-3-(p-tolyl)pyrrolidine-2-carboxylate: yellow oil; $[\alpha]_D^{23}$ (c 2.41, $CH_2Cl_2$)=−46.8°; $^1$H NMR (400 MHz, $CDCl_3$) δ=1.22 (t, J=7.2 Hz, 3H), 2.36 (s, 3H), 2.65 (dd, J=17.6 Hz, 9.6 Hz, 1H), 3.02 (dd, J=17.6 Hz, 9.6 Hz, 1H), 3.53-3.59 (m, 1H), 4.15-4.28 (m, 2H), 4.70 (d, J=6.0 Hz, 1H), 7.20 (d, J=7.6 Hz, 2H), 7.35-7.44 (m, 4H), 7.53 (t, J=7.2 Hz, 1H), 7.85 (d, J=7.2 Hz, 2H), 8.67 (bs, 1H); $^{13}$C NMR (100 MHz, $CDCl_3$) δ=172.9, 171.0, 166.0, 138.3, 137.4, 132.5, 131.3, 129.8, 128.7, 127.6, 127.1, 67.4, 61.9, 40.3, 36.8, 21.1, 14.1; HRMS(ESI) calcd for $C_{21}H_{23}N_2O_4$ (M+H)$^+$: 367.1658, Found: 367.1657; 97:3 e.r. as determined by HPLC [Chiralcel IA, 75:20:5 hexanes/(hexanes:i-PrOH:$CH_3OH$=90:5:5)/i-PrOH, 0.7 mL/min)], $t_r$ (major)=108.1 min, $t_r$ (minor)=86.0 min.

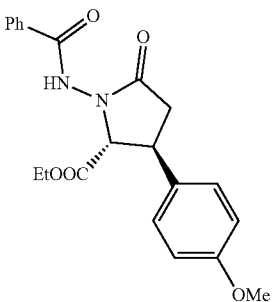

7f

Example 50: (2R,3S)-ethyl1-benzamido-3-(4-methoxyphenyl)-5-oxopyrrolidine-2-carboxylate: yellow oil; $[\alpha]_D^{23}$ (c 2.2, $CH_2Cl_2$)=−69.9°; $^1$H NMR (400 MHz, $CDCl_3$) δ=1.23 (t, J=7.2 Hz, 3H), 2.65 (dd, J=18.0 Hz, 6.8 Hz, 1H), 2.99 (dd, J=17.6 Hz, 9.6 Hz, 1H), 3.51-3.57 (m, 1H), 3.82 (s, 3H), 4.16-4.29 (m, 2H), 4.68 (d, J=5.6 Hz, 1H), 6.93 (d, J=8.8 Hz, 2H), 7.39-7.47 (m, 4H), 7.55 (t, J=7.2 Hz, 1H), 7.85 (d, J=7.2 Hz, 2H), 8.42 (bs, 1H); $^{13}$C NMR (100 MHz, CDCl$_3$) δ=172.6, 171.0, 166.0, 159.1, 133.5, 132.6, 131.4, 128.8, 128.2, 127.5, 114.5, 67.5, 61.9, 55.3, 39.9, 36.8, 21.8, 14.2; HRMS(ESI) calcd for C$_{21}$H$_{23}$N$_2$O$_5$ (M+H)$^+$: 383.1607, Found: 383.1608; 97:3 e.r. as determined by HPLC [Chiralcel IA, 70:20:10 hexanes/(hexanes:i-PrOH:CH$_3$OH=90:5:5)/i-PrOH, 0.7 mL/min)], t$_r$ (major)=82.2 min, t$_r$ (minor)=73.0 min.

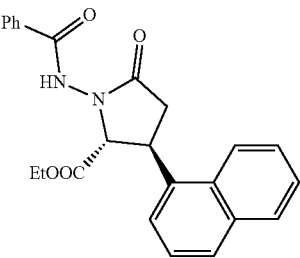

7g

Example 51: (2R,3S)-ethyl1-benzamido-3-(naphthalen-1-yl)-5-oxopyrrolidine-2-carboxylate: yellow oil; [α]$_D^{23}$ (c 2.08, CH$_2$Cl$_2$)=−11.1°; $^1$H NMR (400 MHz, CDCl$_3$) δ=1.15 (t, J=7.2 Hz, 3H), 2.79 (dd, J=17.2 Hz, 5.6 Hz, 1H), 3.21 (dd, J=17.6 Hz, 5.6 Hz, 1H), 4.16-4.26 (m, 2H), 4.43-4.48 (m, 1H), 5.02 (d, J=4.8 Hz, 1H), 7.44 (t, J=7.6 Hz, 2H), 7.52-7.61 (m, 4H), 7.83-7.94 (m, 5H), 8.11 (d, J=8.4 Hz, 1H), 8.70 (bs, 1H); $^{13}$C NMR (100 MHz, CDCl$_3$) δ=172.8, 171.3, 166.2, 136.8, 134.1, 132.6, 131.4, 130.9, 129.3, 128.7, 128.3, 127.6, 126.6, 126.0, 125.8, 122.6, 66.4, 62.1, 36.3, 14.0; HRMS(ESI) calcd for C$_{24}$H$_{23}$N$_2$O$_4$ (M+H)$^+$: 403.1658, Found: 403.1659; 97:3 e.r. as determined by HPLC [Chiralcel IA, 90:10 hexanes/i-PrOH, 0.7 mL/min)], t$_r$ (major)=93.4 min, t$_r$ (minor)=78.9 min.

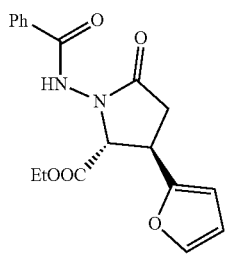

7h

Example 52: (2R,3R)-ethyl 1-benzamido-3-(furan-2-yl)-5-oxopyrrolidine-2-carboxylate: colorless oil; [α]$_D^{23}$ (c 1.55, CH$_2$Cl$_2$)=−40.8°; $^1$H NMR (400 MHz, CDCl$_3$) δ=1.26 (t, J=7.2 Hz, 3H), 2.80-2.95 (m, 2H), 3.74 (dd, J=15.2 Hz, 7.2 Hz, 1H), 4.19-4.31 (m, 2H), 4.80 (d, J=6.4 Hz, 1H), 6.36-6.39 (m, 2H), 7.43 (t, J=7.6 Hz, 3H), 7.53 (t, J=7.6 Hz, 1H), 7.83 (d, J=7.6 Hz, 2H), 8.48 (bs, 1H); $^{13}$C NMR (100 MHz, CDCl$_3$) δ=172.1, 170.4, 165.8, 152.5, 142.4, 132.6, 131.3, 128.7, 127.5, 110.6, 106.8, 64.7, 62.1, 34.4, 33.6, 14.1; HRMS(ESI) calcd for C$_{18}$H$_{19}$N$_2$O$_5$ (M+H)$^+$: 343.1294, Found: 343.1295; 95:5 e.r. as determined by HPLC [Chiralcel IA, 70:20:10 hexanes/(hexanes:i-PrOH:CH$_3$OH=90:5:5)/i-PrOH, 0.7 mL/min)], t$_r$ (major)=63.7 min, t$_r$ (minor)=56.4 min.

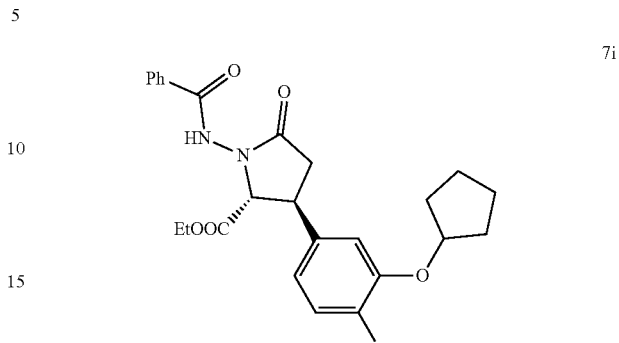

7i

Example 53: (2R,3S)-ethyl1-benzamido-3-(3-(cyclopentyloxy)-4-methoxyphenyl)-5-oxopyrrolidine-2-carboxylate: yellow oil; [α]$_D^{23}$ (c 0.63, CH$_2$Cl$_2$)=−66.3°; $^1$H NMR (400 MHz, CDCl$_3$) δ=1.24 (t, J=7.2 Hz, 3H), 1.61-1.63 (m, 2H), 1.86-2.02 (m, 6H), 2.63 (dd, J=17.2 Hz, 6.0 Hz, 1H), 2.99 (dd, J=17.2, 6.0 Hz, 1H), 3.48-3.53 (m, 1H), 3.85 (s, 3H), 4.18-4.29 (m, 2H), 4.69 (d, J=4.8 Hz, 1H), 4.90-4.92 (m, 1H), 6.86 (d, J=8.0 Hz, 1H), 6.96 (d, J=8.0 Hz, 1H), 7.06 (s, 1H), 7.46 (t, J=7.6 Hz, 2H), 7.56 (t, J=7.6 Hz, 1H), 7.84 (d, J=7.2 Hz, 2H), 8.28 (bs, 1H); $^{13}$C NMR (100 MHz, CDCl$_3$) δ=173.1, 171.0, 166.1, 150.7, 147.3, 134.2, 132.5, 128.6, 127.6, 119.3, 115.1, 110.7, 80.6, 67.5, 51.9, 56.4, 40.2, 36.9, 32.9, 24.1, 14.2, HRMS(ESI) calcd for C$_{26}$H$_{31}$N$_2$O$_6$ (M+H)$^+$: 467.2182, Found: 467.2813; 96:4 e.r. as determined by HPLC (Chiralcel IA, 93:7 hexanes/i-PrOH, 0.7 mL/min), t$_r$ (major)=94.6 min, t$_r$ (minor)=73.1 min.

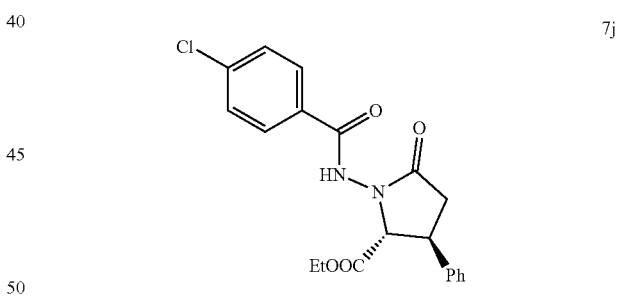

7j

Example 54: (2R,3S)-ethyl1-(4-chlorobenzamido)-5-oxo-3-phenylpyrrolidine-2-carboxylate: white solid, trans:cis=7:1, 70% yield of both isomers; [α]$_D^{23}$ (c 1.25, CH$_2$Cl$_2$)=−26.8°. $^1$H NMR (400 MHz, CDCl$_3$) δ=1.22 (t, J=7.2 Hz, 3H), 2.72 (dd, J=17.6 Hz, 6.8 Hz, 1H), 3.09 (dd, J=17.6 Hz, 9.6 Hz, 1H), 3.59-3.64 (m, 1H), 4.15-4.28 (m, 2H), 4.70 (d, J=5.6 Hz, 1H), 7.32-7.48 (m, 7H), 7.77 (d, J=8.8 Hz, 2H), 9.19 (bs, 1H); $^{13}$C NMR (100 MHz, CDCl$_3$) δ=173.4, 170.8, 164.9, 141.2, 129.2, 129.0, 128.9, 127.8, 127.2, 67.3, 61.9, 40.6, 36.8, 14.1; HRMS(ESI) calcd for C$_{20}$H$_{20}$N$_2$O$_4$Cl (M+H)$^+$: 387.1112, Found: 387.1111; 96:4 e.r. as determined by HPLC [Chiralcel IA, 73:20:7 hexanes/(hexanes:i-PrOH:CH$_3$OH=90:5:5)/i-PrOH, 0.7 mL/min)], t$_r$ (major)=125.9 min, t$_r$ (minor)=100.0 min.

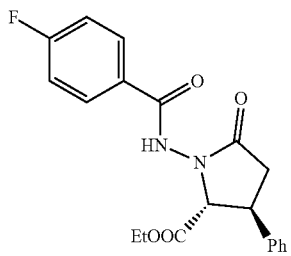

7k

Example 55: (2R,3S)-ethyl 1-(4-fluorobenzamido)-5-oxo-3-phenylpyrrolidine-2-carboxylate: White solid, trans:cis=5:1, 61% yield of both isomers; $[\alpha]_D^{23}$(c 1.0, CHCl$_3$)=−59.6; $^1$H NMR (400 MHz, CDCl$_3$) δ 9.19 (s, 1H), 7.89-7.86 (m, 2H), 7.50-7.40 (m, 4H), 7.35-7.27 (m, 1H), 7.09-7.01 (m, 2H), 4.72 (d, J=5.6 Hz, 1H), 4.36-4.10 (m, 2H), 3.65-3.60 (m, 1H), 3.10 (dd, J=17.6, 10.0 Hz, 1H), 2.93 (dd, J=17.2, 6.4 Hz, 1H), 1.22 (t, J=7.2, 3H); $^{13}$C NMR (100 MHz, CDCl$_3$) δ 173.6, 171.0, 166.8, 165.0, 164.3, 141.5, 130.3 (d, J=9.0 Hz), 129.3, 128.0, 127.5 (d, J=13.0 Hz), 116.0 (d, J=22.0 Hz), 69.6, 62.1, 40.8, 37.0. 14.3; HRMS for C$_{20}$H$_{20}$N$_2$O$_4$ [M+1]$^+$ Calculated: 371.1407, Found: 371.1398; 96:4 e.r. as determined by HPLC [Chiralcel IA, 75:20:5 hexanes/(hexanes:i-PrOH:CH$_3$OH=90:5:5)/i-PrOH, 0.7 mL/min)], t$_r$ (major)=146.8 min, t$_r$ (minor)=111.6 min.

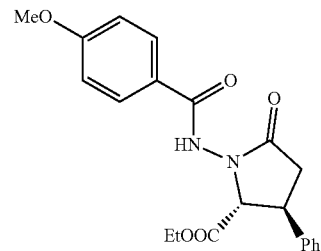

7m

Example 57: (2R,3S)-ethyl 1-(4-methoxybenzamido)-5-oxo-3-phenylpyrrolidine-2-carboxylate: White solid, trans cis=5:1, 70% yield of both isomers; $[\alpha]_D^{23}$ (c 0.3, CHCl$_3$)=−58.3; $^1$H NMR (400 MHz, CDCl$_3$) δ 8.44 (s, 1H), 7.81-7.79 (m, 2H), 7.47 (d, J=7.6 Hz, 2H), 7.39 (t, J=7.2 Hz, 2H), 7.32-7.25 (m, 1H), 6.93-6.88 (m, 2H), 4.71 (d, J=5.6 Hz, 1H), 4.29-4.10 (m, 2H), 3.84 (s, 3H), 3.59-3.54 (m, 1H), 3.02 (dd, J=17.6, 10.0 Hz, 1H), 2.67 (dd, J=17.6, 6.8 Hz, 1H), 1.20 (t, J=7.2, 3H); $^{13}$C NMR (100 MHz, CDCl$_3$) δ 173.0, 171.2, 165.8, 163.3, 141.7, 129.7, 129.3, 127.9, 127.4, 123.8, 114.2, 67.5, 62.1, 55.7, 40.8, 37.0, 14.4; HRMS for C$_{21}$H$_{23}$N$_2$O$_5$ [M+1]$^+$ Calculated: 383.1607, Found: 383.1637; HPLC analysis: 97:3 e.r. as determined by HPLC [Chiralcel IA, 65:30:5 hexanes/(hexanes:i-PrOH:CH$_3$OH=90:5:5)/i-PrOH, 0.7 mL/min)], t$_r$ (major)=96.6 min, t$_r$ (minor)=103.0 min.

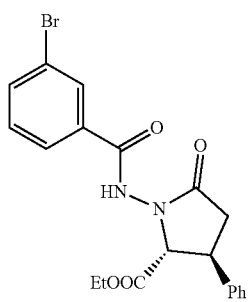

7l

Example 56: (2R,3S)-ethyl 1-(3-bromobenzamido)-5-oxo-3-phenylpyrrolidine-2-carboxylate: White solid, trans:cis=5:1, 59% yield of both isomers; $[\alpha]_D^{23}$ (c 1.1, CHCl$_3$)=−45.3; $^1$H NMR (400 MHz, CDCl$_3$) δ 9.09 (s, 1H), 7.97 (s, 1H), 7.77 (d, J=8.0 Hz, 1H), 7.65 (d, J=8.4 Hz, 1H), 7.47 (d, J=7.6 Hz, 2H), 7.40 (t, J=7.6 Hz, 2H), 7.34-7.26 (m, 2H), 4.71 (d, J=5.6 Hz, 1H), 4.31-4.09 (m, 2H), 3.63-3.58 (m, 1H), 3.06 (dd, J=17.2, 9.6 Hz, 1H), 2.70 (dd, J=17.6, 6.8 Hz, 1H), 1.22 (t, J=7.2, 3H); $^{13}$C NMR (100 MHz, CDCl$_3$) δ 173.3, 171.0, 164.7, 141.5, 135.6, 133.2, 131.1, 130.4, 129.3, 127.9, 127.4, 126.2, 123.1, 67.4, 62.2, 40.8, 36.9, 14.3; HRMS for C$_{20}$H$_{20}$N$_2$O$_4$Br [M+1]$^+$ Calculated: 431.0606, Found: 431.0609; HPLC analysis: 96:4 e.r. as determined by HPLC [Chiralcel IA, 75:20:5 hexanes/(hexanes:i-PrOH:CH$_3$OH=90:5:5)/i-PrOH, 0.7 mL/min)], t$_r$ (major)=47.4 min, t$_r$ (minor)=52.9 min.

7n

Example 58: (2R,3S)-ethyl 1-(4-bromobenzamido)-5-oxo-3-phenylpyrrolidine-2-carboxylate: White solid, trans:cis=5:1, 65% yield of both isomers; $[\alpha]_D^{23}$ (c 0.2, CHCl$_3$)=−10; $^1$H NMR (400 MHz, CDCl$_3$) δ 8.91 (s, 1H), 7.68 (d, J=8.4 Hz, 2H), 7.53 (d, J=8.4 Hz, 2H), 7.46 (d, J=7.6 Hz, 2H), 7.39-7.25 (m, 3H), 4.69 (d, J=5.6 Hz, 1H), 4.29-4.10 (m, 2H), 3.62-3.56 (m, 1H), 3.05 (dd, J=17.6, 9.6 Hz, 1H), 2.69 (dd, J=17.6, 6.4 Hz, 1H), 1.21 (t, J=7.2, 3H); $^{13}$C NMR (100 MHz, CDCl$_3$) δ 173.2, 171.0, 165.3, 141.5, 132.2, 130.2, 129.4, 129.3, 128.0, 127.7, 127.4, 67.5, 62.2, 40.8, 36.9, 14.3; HRMS for C$_{20}$H$_{20}$N$_2$O$_4$Br [M+1]$^+$ Calculated: 431.0606, Found: 431.0626; 95:5 e.r. as determined by HPLC [Chiralcel IA, 65:30:5 hexanes/(hexanes:i-PrOH:CH$_3$OH=90:5:5)/i-PrOH, 0.7 mL/min)], t$_r$ (major)=66.1 min, t$_r$ (minor)=60.0 min.

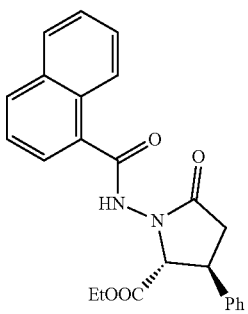

7o

Example 59: (2R,3S)-ethyl 1-(1-naphthamido)-5-oxo-3-phenylpyrrolidine-2-carboxylate: White solid, trans:cis=6:1, 71% yield of both isomers; $[\alpha]_D^{23}$ (c 0.9, CHCl$_3$)=−15; $^1$H NMR (400 MHz, CDCl$_3$) δ 8.48 (d, J=8.0 Hz, 1H), 8.00 (d, J=8.0 Hz, 1H), 7.90 (d, J=7.6 Hz, 1H), 7.79 (d, J=6.8 Hz 1H), 7.62-7.41 (m, 7H), 7.36-7.34 (m, 1H), 4.85 (d, J=5.6 Hz, 1H), 4.29-4.18 (m, 2H), 3.65-3.59 (m, 2H), 3.03 (dd, J=17.6, 8.0 Hz, 1H), 2.74 (dd, J=17.6, 6.8 Hz, 1H), 1.24 (t, J=7.2 Hz, 3H); $^{13}$C NMR (mixture of both isomers, 100 MHz, CDCl$_3$) δ 172.6, 171.1, 168.3, 141.5, 133.9, 132.1, 130.7, 130.5, 129.4, 128.7, 128.6, 128.0, 127.8, 127.4, 127.0, 126.4, 125.5, 125.2, 124.8, 124.7, 67.5, 62.2, 62.0, 40.9, 36.9. 14.4; HRMS for C$_{24}$H$_{23}$N$_2$O$_4$ [M+1]$^+$ Calculated: 403.1658, Found: 403.1643; 95:5 e.r. as determined by HPLC [Chiralcel IA, 75:20:5 hexanes/(hexanes:i-PrOH:CH$_3$OH=90:5:5)/i-PrOH, 0.7 mL/min)], t$_r$ (major)=107.2 min, t$_r$ (minor)=120.6 min.

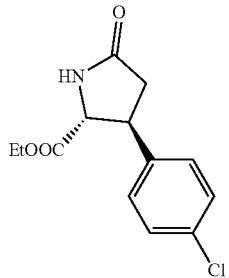

8c

Example 60: (2R,3S)-ethyl 3-(4-chlorophenyl)-5-oxopyrrolidine-2-carboxylate: yellow oil; $[\alpha]_D^{23}$ (c 0.67, CH$_2$Cl$_2$)=−66.6°; $^1$H NMR (400 MHz, CDCl$_3$) δ=1.27 (t, J=7.2 Hz, 3H), 2.49 (dd, J=17.6 Hz, 6.8 Hz, 1H), 2.86 (dd, J=17.2, 9.6 Hz, 1H), 3.68-3.74 (m, 1H), 4.17-4.27 (m, 3H), 6.14 (bs, 1H), 7.23 (d, J=8.0 Hz, 2H), 7.34 (d, J=8.0 Hz, 2H); $^{13}$C NMR (100 MHz, CDCl$_3$) δ=176.6, 171.1, 140.3, 133.3, 129.2, 128.4, 62.9, 61.9, 43.3, 38.0, 14.1; HRMS(ESI) calcd for C$_{13}$H$_{15}$NO$_3$Cl (M+H)$^+$: 268.0740, Found: 268.0743; 96:4 e.r. as determined by HPLC [Chiralcel IB, 95:5 hexanes/i-PrOH, 0.7 mL/min)], t$_r$ (major)=60.4 min, t$_r$ (minor)=53.8 min.

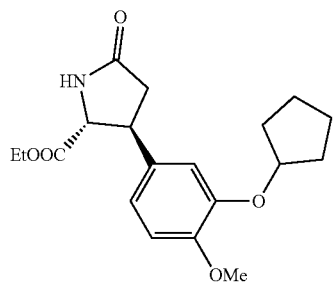

7i-2

Example 61: (2R,3S)-ethyl3-(3-(cyclopentyloxy)-4-methoxyphenyl)-5-oxopyrrolidine-2-carboxylate: yellow oil; $[\alpha]_D^{23}$ (c 1.42, CH$_2$Cl$_2$)=−38.2°; $^1$H NMR (400 MHz, CDCl$_3$) δ=1.27 (d, J=7.2 Hz, 3H), 1.60-1.66 (m, 2H), 1.81-1.92 (m, 6H), 2.51 (dd, J=17.2 Hz, 6.4 Hz, 1H), 2.84 (dd, J=17.2, 6.4 Hz, 1H), 3.62-3.68 (m, 1H), 3.84 (s, 3H), 4.18-4.27 (m, 3H), 4.75-4.78 (m, 1H), 6.17 (bs, 1H), 6.80-6.85 (m, 3H); $^{13}$C NMR (100 MHz, CDCl$_3$) δ=176.4, 171.3, 149.5, 148.0, 134.3, 119.0, 113.8, 112.3, 80.6, 63.1, 61.8, 56.1, 43.5, 37.9, 32.8, 24.0, 14.2; HRMS(ESI) calcd for C$_{19}$H$_{26}$NO$_5$ (M+H)$^+$: 348.1811, Found: 348.1813; 96:4 e.r. as determined by HPLC [Chiralcel IA, 90:10 hexanes/i-PrOH, 0.7 mL/min)], t$_r$ (major)=28.2 min, t$_r$ (minor)=24.6 min.

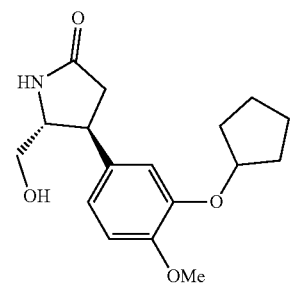

7i-3

Example 62: (4S,5R)-4-(3-(cyclopentyloxy)-4-methoxyphenyl)-5-(hydroxymethyl)pyrrolidin-2-one: colorless oil; $[\alpha]_D^{23}$ (c 0.52, CH$_2$Cl$_2$)=−14.6°; $^1$H NMR (400 MHz, CDCl$_3$) δ=1.59 (dd, J=7.0, 5.1 Hz, 2H), 2.02-1.69 (m, 6H), 2.53 (dd, J=17.2, 8.8 Hz, 1H), 2.77 (dd, J=17.2, 9.3 Hz, 1H), 3.36-3.12 (m, 1H), 3.50-3.55 (m, 1H), 3.76 (d, J=7.3 Hz, 2H), 3.81 (s, 3H), 4.14 (brs, 1H), 4.76 (dd, J=5.9, 2.7 Hz, 1H), 6.86-6.60 (m, 3H), 7.46 (brs, 1H); $^{13}$C NMR (100 MHz, CDCl$_3$) δ=24.0, 32.79, 32.82, 39.4, 42.0, 56.2, 64.0, 64.4, 80.6, 112.3, 114.3, 119.3, 133.9, 147.9, 149.3, 178.0; HRMS(ESI) calcd for C$_{17}$H$_{24}$NO$_4$ (M+H)$^+$: 306.1705, Found: 306.1705.

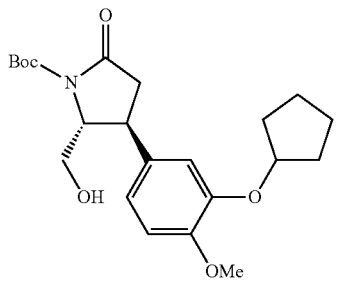

Example 63: (2R,3S)-tert-butyl3-(3-(cyclopentyloxy)-4methoxyphenyl)-2-(hydroxymethyl)-5-oxopyrrolidine-1-carboxylate: colorless oil; $[\alpha]_D^{23}$ (c 0.4, $CH_2Cl_2$)=–8.5°; $^1H$ NMR (500 MHz, $CDCl_3$) δ=1.48 (s, 9H), 1.60-1.63 (m, 2H), 1.82-1.94 (m, 6H), 2.53 (dd, J=17.3, 9.0 Hz, 1H), 2.79 (dd, J=17.3, 9.3 Hz, 1H), 3.22 (dd, J=16.5, 9.0 Hz, 1H), 3.83 (s, 3H), 3.85-3.87 (m, 1H), 3.94 (dd, J=11.0, 6.0 Hz, 1H), 4.25 (dd, J=11.5, 3.0 Hz, 1H), 4.76-4.78 (m, 1H), 6.77 (dd, J=12.0, 2.0 Hz, 2H), 6.82 (d, J=8.5 Hz, 1H); $^{13}CNMR$ (125 Hz, $CDCl_3$): δ=24.0, 27.7, 32.8, 38.7, 42.6, 56.1, 60.8, 68.0, 80.6, 82.9, 112.3, 113.9, 119.3, 133.1, 148.1, 149.5, 153.3, 176.2; HRMS(ESI) calcd for $C_{22}H_{32}NO_6$ $(M+H)^+$: 406.2230, Found: 406.2236. 96:4 e.r. as determined by HPLC [Chiralcel IA, 90:10 hexanes/i-PrOH, 0.7 mL/min)], $t_r$ (major)=15.7 min, $t_r$ (minor)=11.3 min.

While particular preferred and alternative embodiments of the present invention have been disclosed, it will be apparent to one of ordinary skill in the art that many various modifications and extensions of the above described technology may be implemented using the teaching of this invention described herein. All such modifications and extensions are intended to be included within the true spirit and scope of the invention as discussed in the appended claims.

REFERENCES

1. Reed, P. E. & Katzenellenbogen, J. A. Beta-Substituted Beta-Phenylpropionyl Chymotrypsins-Structural and Stereochemical Features in Stable Acyl Enzymes. *J. Med. Chem.* 1991, 34, 1162-1176.
2. Kerr, M. S., de Alaniz, J. R. & Rovis, T. An efficient synthesis of achiral and chiral 1,2,4-triazolium salts: Bench stable precursors for N-heterocyclic carbenes. *J. Org. Chem.* 2005, 70, 5725-5728.
3. Matsuoka, Y., Ishida, Y., Sasaki, D. & Saigo, K. Cyclophane-Type Imidazolium Salts with Planar Chirality as a New Class of N-Heterocyclic Carbene Precursors. *Chem.-Eur. J.* 2008, 14, 9215-9222.
4. Raup, D. E. A., Cardinal-David, B., Holte, D., Scheidt, K. A. Cooperative Catalysis by Carbenes and Lewis Acids in a Highly Stereoselective Route to β-Lactams. *Nat. Chem.* 2010, 2, 766-771.
5. Oba, M., Saegusa, T., Nishiyama, N. & Nishiyama, K. Synthesis of non-proteinogenic amino acids using Michael addition to unsaturated orthopyroglutamate derivative. *Tetrahedron* 2009, 65, 128-133.
6. Diaz, A. et al., A stereoselective synthesis of (R)-(-)-rolipram from L-glutamic acid. *Synthesis*, 1997, 559-562.
7. Chiang, P., Kaeobamrung, J. & Bode, J. W. Enantioselective, cyclopentene-forming annulations via NHC-catalyzed benzoin-oxy-Cope reactions. *J. Am. Chem. Soc.* 2007, 129, 3520-3521.

The invention claimed is:

1. A method for synthesizing a compound of Formula (Ia)

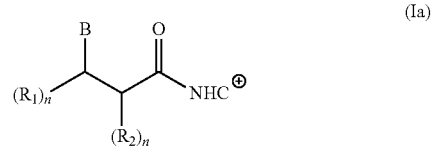

wherein n is 2;

$R_1$ is 2-furyl, propyl, methyl, phenyl, p-tolyl, p-anisyl, p-fluorophenyl, p-chlorophenyl, p-bromophenyl, or naphthyl, $R_2$ is hydrogen;

B is

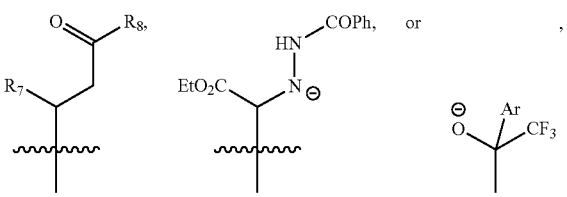

wherein $R_7$ is phenyl, p-tolyl, p-chlorophenyl, p-bromophenyl, naphthyl, 2-thiofuryl, o-nitrophenyl, m-nitrophenyl, or p-nitrophenyl, wherein $R_8$ is phenyl, 2-furyl, p-tolyl, p-chlorophenyl or p-bromophenyl, wherein Ar is phenyl, p-tolyl, p-chlorophenyl, p-bromophenyl, or 2-thiofuryl; and $NHC^\oplus$ is

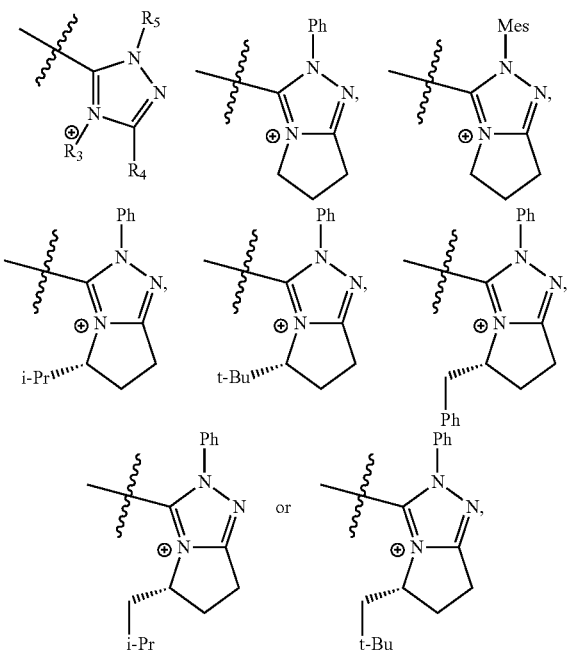

comprising:
(i) activating a compound of Formula (IIa)

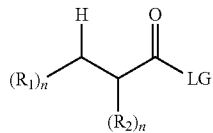

wherein
LG is —O—C$_6$H$_4$-para-NO$_2$;
by reacting said compound of Formula (IIa) with one of the compounds of Formula (III) in the presence of DBU (1,8-Diazabicyclo[5.4.0]undec-7-en)

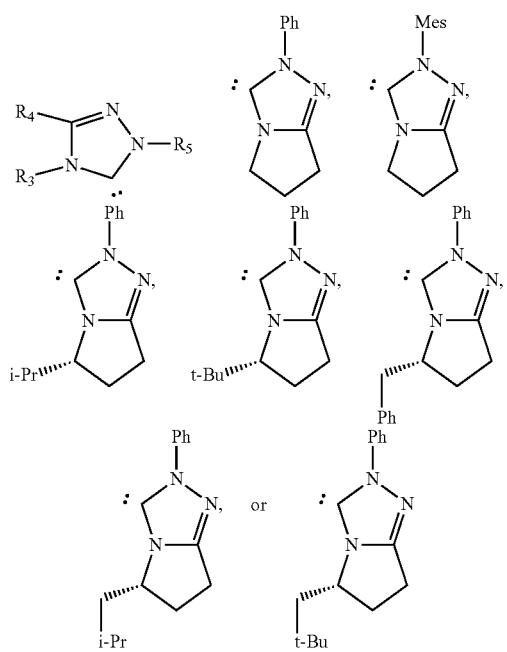

to obtain a compound of Formula (IVa)

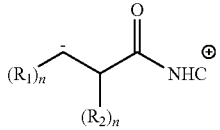

and
(ii) reacting the compound of Formula (IVa) with an electrophile to obtain the compound of Formula (Ia), wherein the electrophile is selected from the group consisting of

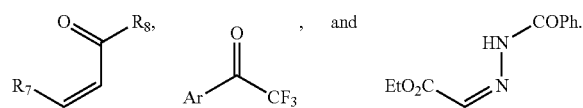

2. The method according to claim 1, wherein NHC$^⊕$ is selected from the group consisting of

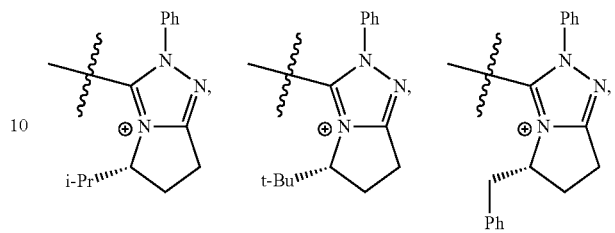

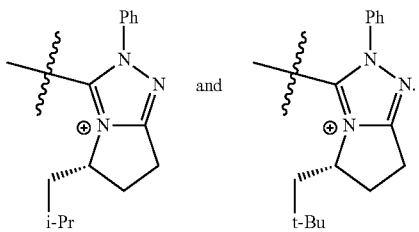

3. The method according to claim 2, wherein NHC$^⊕$ is selected from the group consisting of

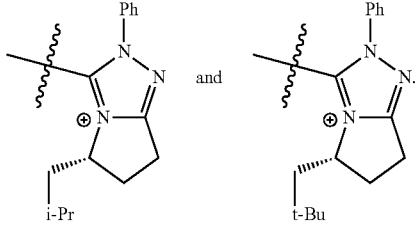 [SMILES: *c1n(-c2ccccc2)nc2[n+]1[C@@H](CC(C)C)CC2 ; "and" ; *c1n(-c2ccccc2)nc2[n+]1[C@@H](CC(C)(C)C)CC2]

4. The method according to claim 1, wherein NHC$^⊕$ is selected from the group consisting of

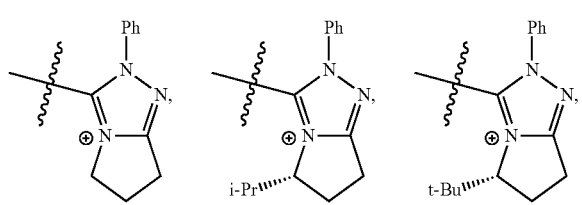

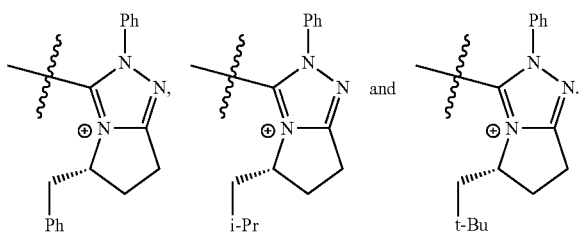

5. The method according to claim 1, wherein the compound of Formula (III) is synthesized from any of the following compounds selected from the group consisting of

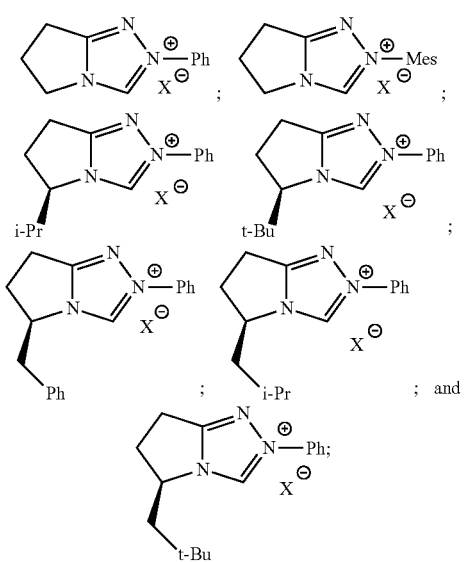

wherein X is $BF_4^-$.

6. The method according to claim 1, wherein the compound of Formula (III) is generated in situ from any of the following compounds selected from the group consisting of

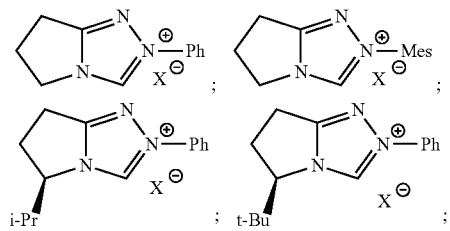

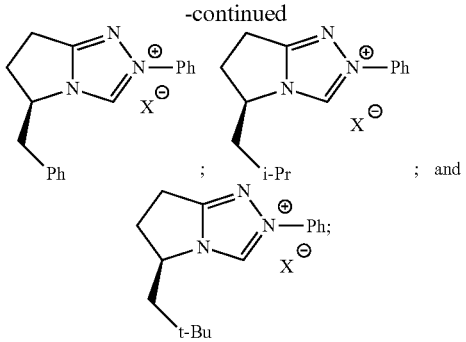

wherein X is $BF_4^-$

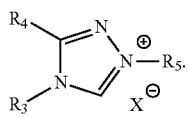

7. The method according to claim 1, wherein the method is carried out in a solvent selected from the group consisting of tent-Butanol, toluene, THF, $CH_3CN$, $CH_2Cl_2$, dioxane, and ethyl acetate.

8. The method according to claim 1, wherein the reaction temperature of steps (i) and (ii) is 25° C. or 40° C.

9. The method according to claim 1, wherein the reaction time is about 24 hours.

10. The method according to claim 1, wherein a molecular sieve is present during the reaction.

11. The method according to claim 10, wherein the molecular sieve has apertures of a size of approximately 4 Å.

12. The method according to claim 1, wherein the method comprises further reaction steps selected from catalyst regeneration, michael reaction, aldol reaction, lactonization, and/or decarboxylation.

* * * * *